(12) United States Patent
Rothberg et al.

(10) Patent No.: US 10,551,624 B2
(45) Date of Patent: Feb. 4, 2020

(54) COMPACT BEAM SHAPING AND STEERING ASSEMBLY

(71) Applicant: Quantam-Si Incorporated, Guilford, CT (US)

(72) Inventors: Jonathan M. Rothberg, Guilford, CT (US); Paul E. Glenn, Wellesley, MA (US); Jonathan C. Schultz, Guilford, CT (US); Benjamin Cipriany, Branford, CT (US)

(73) Assignee: Quantum-Si Incorporated, Guilford, CT (US)

( * ) Notice: Subject to any disclaimer, the term of this patent is extended or adjusted under 35 U.S.C. 154(b) by 0 days.

(21) Appl. No.: 15/842,720

(22) Filed: Dec. 14, 2017

(65) Prior Publication Data

US 2018/0173000 A1 Jun. 21, 2018

Related U.S. Application Data

(60) Provisional application No. 62/435,679, filed on Dec. 16, 2016.

(51) Int. Cl.
*G02B 27/09* (2006.01)
*G02B 6/34* (2006.01)
*G02B 7/00* (2006.01)

(52) U.S. Cl.
CPC .......... *G02B 27/0927* (2013.01); *G02B 6/34* (2013.01); *G02B 7/005* (2013.01); *G02B 27/0911* (2013.01); *G02B 27/0916* (2013.01); *G02B 27/0944* (2013.01); *G02B 27/0972* (2013.01)

(58) Field of Classification Search
CPC .............................. G02B 27/0927; G02B 6/34
See application file for complete search history.

(56) References Cited

U.S. PATENT DOCUMENTS

| 5,854,651 | A | * | 12/1998 | Kessler | ...................... | B41J 2/45 |
| | | | | | | 347/241 |
| 6,205,266 | B1 | * | 3/2001 | Palen | ................... | G02B 6/4225 |
| | | | | | | 385/15 |
| 6,473,250 | B1 | * | 10/2002 | Chapman | ........... | G02B 26/0883 |
| | | | | | | 359/669 |
| 6,847,450 | B2 | * | 1/2005 | Richard | ................. | G01B 11/27 |
| | | | | | | 356/139.04 |
| 2001/0050821 | A1 | | 12/2001 | Bickleder et al. | | |
| 2016/0002088 | A1 | | 1/2016 | Mizumura et al. | | |

OTHER PUBLICATIONS

Invitation to Pay Additional Fees for International Application No. PCT/US2017/066348 dated Mar. 8, 2018.

(Continued)

*Primary Examiner* — Sung H Pak
(74) *Attorney, Agent, or Firm* — Wolf, Greenfield & Sacks, P.C.

(57) ABSTRACT

Apparatus and methods for coupling an optical beam from an optical source to a hi-tech system are described. A compact, low-cost beam-shaping and steering assembly may be located between the optical source and hi-tech system and provide automated adjustments to beam parameters such as beam position, beam rotation, and beam incident angles. The beam-shaping and steering assembly may be used to couple an elongated beam to a plurality of optical waveguides.

19 Claims, 10 Drawing Sheets

(56) References Cited

OTHER PUBLICATIONS

International Search Report and Written Opinion for International Application No. PCT/US2017/066348 dated May 4, 2018.
U.S. Appl. No. 15/161,088, filed May 20, 2016, Rothberg et al.
U.S. Appl. No. 15/161,067, filed May 20, 2016, Rothberg et al.
U.S. Appl. No. 15/844,469, filed Dec. 15, 2017, Rothberg et al.
PCT/US2017/066348, Mar. 8, 2018, Invitation to Pay Additional Fees.
PCT/US2017/066348, May 4, 2018, International Search Report and Written Opinion.

* cited by examiner

COMPACT BEAM SHAPING AND STEERING ASSEMBLY

CROSS-REFERENCE TO RELATED APPLICATIONS

This application claims priority to U.S. provisional application No. 62/435,679, filed Dec. 16, 2016 and titled "Compact Beam Shaping and Steering Assembly," which is incorporated by reference in its entirety.

FIELD

The present application is directed to apparatus and methods for coupling an output beam from a laser or other optical source to an input of a hi-tech optical system.

BACKGROUND

Lasers and light-emitting diodes (LEDs) can provide intense radiation at one or more selectable wavelengths that is (are) useful for hi-tech optical systems, such as optical communication systems, bioanalytical systems, medical devices, material processing systems, and defense systems. The output from a laser or LED may be collimated or uncollimated, and the radiation may be pulsed or continuous wave. In some cases, short optical pulses (e.g., optical pulses less than about 1 nanosecond) may be produced by lasers or LEDs and provided to a hi-tech optical system.

Some hi-tech optical systems can include precision optical devices to which the output from the laser or LED must be coupled. One example of a precision optical device is an integrated optical waveguide on a chip. Typically, a spatial mode profile of a beam output from the laser or LED is not well-matched to a spatial mode profile of a fundamental mode, for example, that is supported by the waveguide. Accordingly, one or more optical components may be needed to improve the match between the spatial mode profiles of the beam and receiving optical component of the optical system to which the beam is coupled.

SUMMARY

Some embodiments relate to a beam-shaping and steering assembly comprising a first optical component arranged to transform a first transverse beam shape of an input beam into a second transverse beam shape of a second beam; a second optical component arranged to rotate the second transverse beam shape about an optical axis of the second beam; and a third optical component arranged to adjust one of: a first position or a first directional angle of an output beam at a target location.

Some embodiments relate to a method of coupling a beam from an optical source to a receiving optical component of a system. The method may comprise acts of receiving, by a beam-shaping and steering assembly, the beam from the optical source; transforming, with the beam-shaping and steering assembly, a first transverse beam shape of the beam to a second transverse beam shape of an output beam; positioning, with the beam-shaping and steering assembly, the output beam on the receiving optical component; and adjustably rotating, with the beam-shaping and steering assembly, the second transverse beam shape.

Some embodiments relate to an optical system for coupling a beam of radiation to an apparatus, the optical system comprising three rotary actuators; and three optical components coupled respectively to the three rotary actuators, wherein each rotary actuator has a drive shaft that rotates about a shaft axis to move an optical component of the three optical components, wherein the shaft axes of the three rotary actuators are essentially parallel to a same plane, and wherein actuation of the three optical components by the three rotary actuators alters the beam in three different degrees of freedom.

Some embodiments relate to an optical system for coupling a beam of radiation to an apparatus, the optical system comprising a first optical component supported in an adjustable mount; and a first actuator coupled to the adjustable mount, wherein movement of the first optical component by the first actuator rotates a transverse shape and polarization of an exit beam that exits the first optical component, wherein the rotation of the transverse shape and polarization are about an optical axis that runs centrally along the exit beam.

Some embodiments relate to an optical system for altering a beam of radiation, the optical system may comprise a first optical component supported by an adjustable mount that is configured to rotate the first optical component about a first axis; a rotary actuator having a drive shaft that rotates about a second axis that is not parallel to the first axis; a cam arm connected to the drive shaft; a bearing connected to the cam arm; and a curved surface connected to the adjustable mount, wherein the bearing runs across the curved surface when the rotary actuator is actuated to rotate the first optical component.

Some embodiments relate to an optical beam-steering apparatus comprising a first rotary actuator arranged to rotate a first optical window; a second rotary actuator arranged to rotate a second optical window; and a lens; wherein rotation of the first optical window adjusts a lateral position of an optical beam at a target location and rotation of the second optical window adjusts an incident angle of the beam at the target location without changing the lateral position by more than 10 microns.

Some embodiments relate to an optical beam-steering apparatus comprising three rotatable transparent optical windows arranged to adjust three parameters of an output beam from the beam-steering apparatus in three orthogonal degrees of freedom.

The foregoing and other aspects, implementations, acts, functionalities, features and, embodiments of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

FIG. 1-2 depicts a train of optical pulses that may be produced by an optical source in a hi-tech system, according to some embodiments.

FIG. 1-3 depicts an example of parallel reaction chambers that may be included on a chip mountable within a hi-tech system. The reaction chambers may be excited optically via one or more waveguides and emissions detected by photodetectors formed near each chamber, according to some embodiments.

FIG. 1-4 illustrates time-dependent loss in a waveguide at three different optical powers.

FIG. 1-5 depicts further details of an integrated reaction chamber, optical waveguide, and time-binning photodetector, according to some embodiments.

FIG. 1-6 depicts an example of a biological reaction that may occur within a reaction chamber, according to some embodiments.

FIG. 1-7 depicts emission probability curves for two different fluorophores having different decay characteristics.

FIG. 1-8 depicts time-binning detection of fluorescent emission, according to some embodiments.

FIG. 2-1A depicts coupling of an elongated beam to a plurality of waveguides, according to some embodiments.

FIG. 2-1B depicts coupling of an elongated and rotated beam to a plurality of waveguides, according to some embodiments.

FIG. 2-2A depicts a beam-shaping and steering module, according to some embodiments.

FIG. 2-2B depicts a beam-shaping and steering module mounted to a chassis in an instrument and reinforcing a printed circuit board, according to some embodiments.

FIG. 2-3 depicts optical details of beam shaping and steering components, according to some embodiments.

FIG. 2-4 depicts elements of a rotation mount for an image rotation prism, according to some embodiments.

FIG. 2-5A depicts a mechanical linkage for rotating an optical component, according to some embodiments.

FIG. 2-5B illustrates linearized beam displacement for a mechanical linkage that includes an engineered curved surface to compensate for nonlinearities in the mechanical linkage.

FIG. 2-6 depicts alignment of an optical beam to an optical coupler on a chip, according to some embodiments.

FIG. 2-7 depicts detection and control circuitry for coupling optical pulses from an optical source into multiple waveguides of a bio-optoelectronic chip, according to some embodiments.

Figure 1:
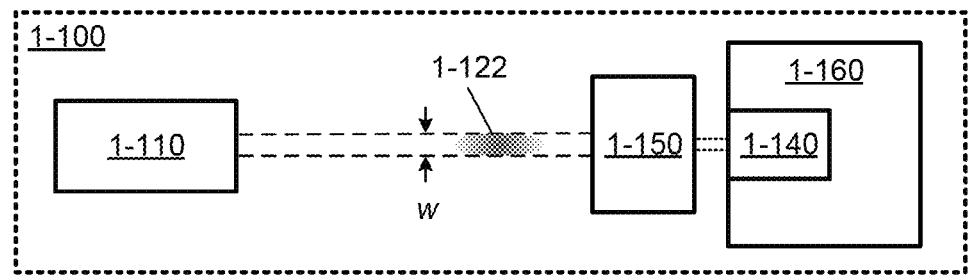
FIG. 1-1 is a block diagram depiction of a hi-tech system, according to some embodiments.

The features and advantages of the present invention will become more apparent from the detailed description set forth below when taken in conjunction with the drawings. When describing embodiments in reference to the drawings, directional references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of features of an embodied device. A device may be embodied using other orientations.

DETAILED DESCRIPTION

I. Introduction

The technology described herein relates to apparatus and methods for coupling optical beams from lasers or light-emitting diodes to hi-tech systems that include precision optical components. A hi-tech system can include one or more precision optical components (e.g., integrated optical waveguide, integrated optical coupler, integrated optical modulator, an optical diffractive element, an optical fiber, etc.) and may further include mechanical components, micromechanical components, electrical circuitry, microfluidic components, microelectromechanical components, bio-microelectromechanical components and/or bio-optoelectronic components. A low-profile, compact, beam-shaping and steering assembly is described that includes five automated adjustments of beam parameters, according to some embodiments. The assembly can also include manual or automated adjustments for beam focus and beam shape. In some implementations, the assembly can be used to couple a round beam from a laser to a linear array of integrated optical waveguides on a bio-optoelectronic chip, and provide nearly uniform power coupling at high efficiency into the plurality of waveguides. The uniformity of coupling across the waveguides can be adjusted by automated manipulation of an optical component in the beam-shaping and steering assembly.

The beam-shaping and steering assembly can be incorporated into portable instrumentation (e.g., time-of-flight imaging instruments, bioanalytical instruments that utilize lifetime-resolved fluorescent detection, genetic sequencing instruments, optical coherence tomography instruments, medical instruments, etc.) to provide precise and stable optical coupling between a compact optical source and precision optical devices of a compact, hi-tech system. The beam-shaping and steering assembly may reduce the effects of vibrations, temperature variations, and manufacturing variations on optical coupling between the optical source and hi-tech system. Examples of optical sources for such embodiments are described in U.S. patent application Ser. No. 15/161,088 filed on May 20, 2016 and titled "Pulsed Laser and Bioadvanced System," and U.S. patent application No. 62/435,688 filed on Dec. 16, 2016 and titled "Compact Mode-Locked Laser Module," which are incorporated herein by reference. Such instrumentation may be readily portable and produced at appreciably lower cost than is the case for conventional instrumentation requiring large optical sources and large optical coupling components. High portability can make such instruments more useful for research, development, clinical use, field deployment, military, and commercial applications.

The inventors have recognized and appreciated that optical sources such as pulsed lasers and LEDs are potentially more useful when the laser or LED and its driving circuitry can output power levels in excess of 100 milliwatts and be made very compact in size, e.g., about the size of an A4 sheet of paper or less with a thickness of about 40 mm or less. When made compact, such optical sources can be incorporated into portable, hi-tech instruments that may be used in, but not limited to, the fields of medical diagnostics, optical communications, massively parallel sample analysis for pharmaceutical development, genetic sequencing, or protein analysis, for example. The term "optical" may be used to refer to ultra-violet, visible, near-infrared, and short-wavelength infrared spectral bands.

The inventors have further recognized and appreciated that it can be advantageous to manufacture such optical sources as a module that can be easily swapped into and out of a portable hi-tech instrument. Such plug-and-play capability can minimize down-time of the instrument, and allow a single source to be used in different instruments. The inventors have further recognized that lasers and LEDs generally have output beams with different beam parameters (e.g., beam size, beam shape, beam collimation, beam direction, transverse beam profile) and hi-tech systems that receive an optical beam can have different requirements for the received beam parameters.

To accommodate differences in beam parameters between an optical source and a hi-tech system, the inventors have conceived of beam-shaping and steering apparatus and associated methods, which are described in further detail below. The beam-shaping and steering apparatus is a compact assembly (e.g., less than half the size of a sheet of A4 paper and less than 40 mm thickness) that can be incorporated into an instrument to adapt an output beam from an optical source to conform to acceptable beam parameters for a hi-tech system to which the optical source is to be coupled. In the following description, embodiments of beam-shaping and steering apparatus are described in connection with a genetic sequencing instrument, which is but one example of a "hi-tech" instrument. It should be appreciated, however, that beam-shaping and steering apparatus of the described embodiments may be used with other types of instruments, whether they include hi-tech or advanced optical technology or not.

In embodiments, a hi-tech instrument 1-100 may comprise an optical source 1-110 mounted within or otherwise coupled to the instrument, as depicted in FIG. 1-1. According to some embodiments, the optical source 1-110 may be a mode-locked laser. A mode-locked laser may include an element (e.g., saturable absorber, acousto-optic modulator, Kerr lens) in the laser cavity, or coupled to the laser cavity, that induces phase locking of the laser's longitudinal frequency modes. In other embodiments, the optical source 1-110 may comprise a gain-switched laser. A gain-switched laser may comprise an external modulator (e.g., pulse-driver circuit) that modulates optical gain in the laser's gain medium.

The instrument 1-100 may include a beam-shaping and steering assembly 1-150 and a hi-tech system 1-160. The beam-shaping and steering assembly 1-150 may include one or more optical components (e.g., lens, mirror, optical filter, beam-shaping optic, attenuator) and be configured to operate on and/or deliver optical pulses 1-122 (or a continuous-wave beam) from the optical source 1-110 to the hi-tech system 1-160.

According to some embodiments, a hi-tech system may direct, collect, and analyze optical signals using optical components, detectors, electronics, and communications hardware. For example, the hi-tech system 1-160 may include optical components that are arranged to direct the optical pulses to at least one sample that is to be analyzed, receive one or more optical signals (e.g., fluorescence, backscattered radiation) from the at least one sample, and produce one or more electrical signals representative of the received optical signals. In some embodiments, the hi-tech system 1-160 may include one or more photodetectors and signal-processing electronics (e.g., one or more microcontrollers, one or more field-programmable gate arrays, one or more microprocessors, one or more digital signal processors, logic gates, etc.) configured to process the electrical signals from the photodetectors. The hi-tech system may also include data transmission hardware configured to transmit and receive data to and from external devices via a data communications link (not shown). In some embodiments, the hi-tech system 1-160 may be configured to receive a bio-optoelectronic chip 1-140, which holds one or more samples to be analyzed. Data signals for sample analysis may be processed partially on chip and/or transmitted to an external processor for analysis. Additionally, data signals indicative of optical coupling to the chip 1-140 and/or sample wells may be provided in real time to the beam-shaping and steering assembly 1-150 to maintain adequate optical coupling in real time during sample analysis, according to some embodiments.

Although the optical pulses 1-122 are depicted as having a single transverse optical mode, in some embodiments, the output from the optical source 1-110 may be multimodal. For example, a transverse output beam profile may have multiple intensity peaks and minima due to multimodal operation of the optical source. In some embodiments, a multimodal output may be homogenized (e.g., by diffusing optics) by one or more optical components in the beam-shaping and steering assembly 1-150. In some implementations, a multimodal output may be coupled to a plurality of fibers or waveguides in the hi-tech system 1-160. For example, each intensity peak of a multimodal output may be coupled to a separate waveguide, or group of waveguides, that connects to the bio-optoelectronic chip 1-140. Allowing an optical source to operate in a multimode state may enable higher output powers from the optical source. In some implementations, the optical source 1-110 may produce pulses 1-122 having other transverse beam profiles such as, but not limited to, top-hat beam profiles, doughnut beam profiles, and line-shaped beam profiles. Such beam profiles may be produced with optical elements having patterned or graded coatings, diffractive optical elements, binary optical elements, axicon lenses, graded-refractive index elements, or a combination of two or more of these optical elements.

For some embodiments, the hi-tech instrument may be configured to receive a removable, packaged, bio-optoelectronic chip 1-140. The chip may include a plurality of reaction chambers, integrated optical components arranged to deliver optical excitation energy to the reaction chambers, and integrated photodetectors arranged to detect fluorescent emission or other optical emission from the reaction chambers. In some implementations, the chip 1-140 may be disposable, whereas in other implementations the chip may be reusable. When the chip is received by the instrument, it may be in electrical and optical communication with the optical source 1-110 and in electrical and/or optical communication with the hi-tech system 1-160. In some embodiments, the bio-optoelectronic chip may be mounted (e.g., via a socket connection) within the system on an electronic circuit board (not shown), such as a printed circuit board (PCB), which may include additional instrument electronics. For example, a PCB on which the bio-optoelectronic chip 1-140 is mounted may include circuitry configured to provide electrical power, one or more clock signals, and control signals to the bio-optoelectronic chip 1-140, and signal-processing circuitry arranged to receive signals representative of emission detected from the reaction chambers on the chip. The PCB may also include circuitry configured to receive feedback signals relating to optical coupling and power levels of the optical pulses 1-122 coupled into waveguides of the bio-optoelectronic chip 1-140. In some embodiments, the PCB may include circuitry configured to provide drive signals to the beam-shaping and steering assembly 1-150 to alter beam parameters for better coupling to the bio-optoelectronic chip 1-140. In some cases, the drive signals may be produced for open-loop control of beam parameters, e.g., adjusted by a user. In some embodiments, the drive signals may be produced as part of a closed-loop feedback control system, e.g., to maintain alignment and/or coupling efficiency of an optical beam. Data returned from the bio-optoelectronic chip may be processed in part or entirely by data-processing circuits in the instrument 1-100, although data may be transmitted via a network connection to one or more remote data processors for data processing, in some implementations.

Figures 1, 2:
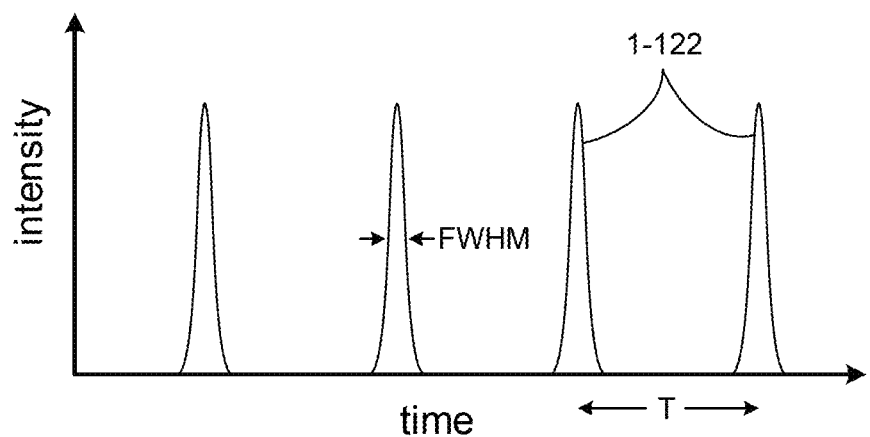

FIG. 1-2 depicts temporal intensity profiles of the output pulses 1-122 from an optical source 1-110, according to some embodiments. In some cases, the peak intensity values of the emitted pulses may be approximately equal, and the profiles may have a Gaussian temporal profile, though other profiles such as a sech² profile may be possible. In some implementations, the pulses may not have symmetric temporal profiles and may have other temporal shapes, such as embodiments using a gain-switched laser. The duration of each pulse may be characterized by a full-width-half-maximum (FWHM) value, as indicated in FIG. 1-2. According to some embodiments of a pulsed optical source, ultrashort optical pulses may be formed and have temporal FWHM values between about 10 picoseconds (ps) and about 100 ps. In other cases, the FWHM values may be shorter than 10 ps or longer than 100 ps.

The output pulses 1-122 may be separated by regular intervals T, according to some embodiments. In some embodiments (e.g., for mode-locked lasers), T may be determined by a round-trip travel time of pulses within a laser cavity of the optical source 1-110. According to some embodiments, the pulse-separation interval T may be between about 1 ns and about 30 ns. In some cases, the pulse-separation interval T may be between about 5 ns and about 20 ns, corresponding to a laser-cavity length between about 0.7 meter and about 3 meters. In some embodiments, a beam-shaping and steering assembly 1-150 may additionally change a pulse length of the optical pulses (e.g., by using frequency-dispersive elements such as gratings and/or optical fibers, diffractive optical elements, or a ring-down cavity). In some embodiments, a beam-shaping and steering assembly may additionally change the pulse-separation interval T (e.g., by splitting the beam received from the optical source 1-110 into different optical paths, adding different delays in the different optical paths, and recombining the optical paths to interleave pulses from the different paths). In some cases, the pulse-separation interval T may not be regular, and the beam-shaping and steering assembly 1-150 may perform its beam-shaping and steering functions regardless of the pulse-separation interval.

For embodiments in which optical pulses 1-122 excite fluorescent emission in a plurality of reaction chambers that is subsequently detected and analyzed in parallel, a desired pulse-separation interval T may be determined by a combination of factors: for example, the number of reaction chambers, fluorescent emission characteristics, and the speed of detection and data-handling circuitry for reading data from the reaction chambers. The inventors have recognized and appreciated that different fluorophores may be distinguished by their different fluorescent decay rates or temporal emission probability curves. Accordingly, there needs to be sufficient pulse-separation interval T to collect adequate statistics for the selected fluorophores that can be used to distinguish between their different emission characteristics. Additionally, if the pulse-separation interval T is too short, the data handling circuitry cannot keep up with the large amount of data being collected by the large number of reaction chambers. The inventors have recognized and appreciated that a pulse-separation interval T between about 5 ns and about 20 ns is suitable for fluorophores that have decay rates up to about 2 ns and for handling data from between about 60,000 and 10,000,000 reaction chambers.

According to some implementations, a beam-shaping and steering module 1-150 may receive output pulses from the optical source 1-110 and be configured to alter at least three beam parameters for improved coupling of a beam from the optical source 1-110 to the hi-tech system 1-160. Beam parameters that may be altered by a beam-shaping and steering module 1-150 include, but are not limited to: beam position at a target location in the hi-tech system, beam direction or incident angles at a target location in the hi-tech system, beam shape, beam collimation, beam rotation about an optical axis of the beam, beam polarization and polarization orientation, beam spectral components, transverse intensity profile of the beam, average beam power, pulse duration, and pulse-separation time.

Figures 1, 2, 3:
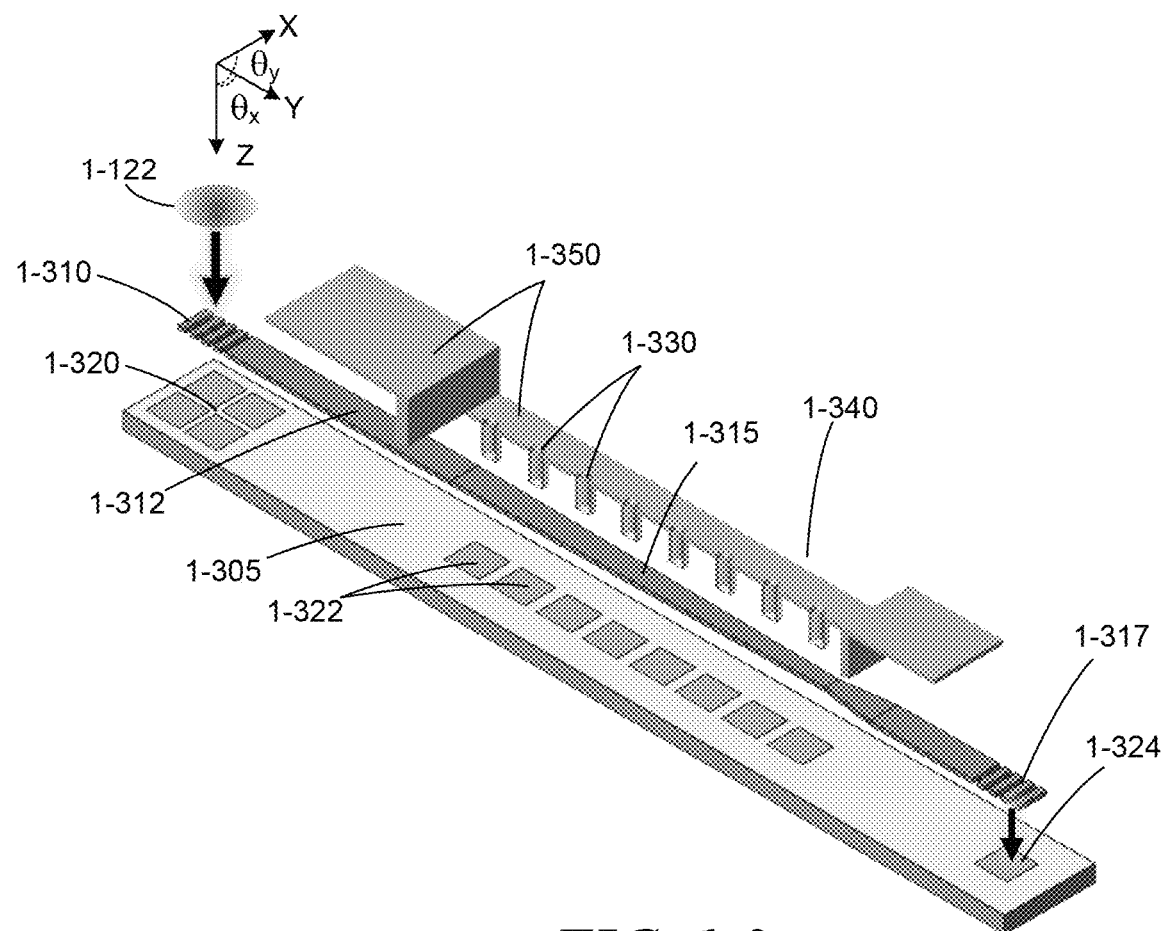

Referring to a bio-analytic embodiment depicted in FIG. 1-3, in some implementations the output pulses 1-122 may be coupled into one or more optical waveguides 1-312 on the bio-optoelectronic chip. In some embodiments, the optical pulses may be coupled to one or more waveguides via a grating coupler 1-310, though coupling to an end of an optical waveguide on the bio-optoelectronic chip may be used in some cases. A quadrant (quad) detector 1-320 may be located on a semiconductor substrate 1-305 (e.g., a silicon substrate) for aiding in alignment of the beam of optical pulses 1-122 to a grating coupler 1-310. The one or more waveguides 1-312 and reaction chambers 1-330 may be integrated on the same semiconductor substrate with intervening dielectric layers (e.g., silicon dioxide layers) between the substrate, waveguide, reaction chambers, and photodetectors 1-322.

Each waveguide 1-312 may include a tapered portion 1-315 or other optical features below the reaction chambers 1-330 to equalize optical power coupled to the reaction chambers along the waveguide. A reducing taper may force more optical energy outside the waveguide's core, increasing coupling to the reaction chambers and compensating for optical losses along the waveguide, including losses for light coupling into the reaction chambers. A second grating coupler 1-317 may be located at an end of each waveguide to direct optical energy to an integrated photodiode 1-324. The integrated photodiode may detect an amount of power coupled down a waveguide and provide a detected signal to feedback circuitry that controls the beam-shaping and steering module 1-150, for example.

The reaction chambers 1-330 may be aligned with the tapered portion 1-315 of the waveguide and recessed in a tub 1-340. There may be time-binning photodetectors 1-322 located on the semiconductor substrate 1-305 for each reaction chamber 1-330. A metal coating and/or multilayer coating 1-350 may be formed around the reaction chambers and above the waveguide to prevent optical excitation of fluorophores that are not in the reaction chambers (e.g., dispersed in a solution above the reaction chambers). The metal coating and/or multilayer coating 1-350 may be raised beyond edges of the tub 1-340 to reduce absorptive losses of the optical energy in the waveguide 1-312 at the input and output ends of each waveguide.

According to some embodiments, there may be a plurality of rows of waveguides, reaction chambers, and time-binning photodetectors on the bio-optoelectronic chip 1-140 so that massively parallel analyses of samples can be carried out. For example, there may be 128 rows, each having 512 reaction chambers, for a total of 65,536 reaction chambers in some implementations. Other implementations may include fewer or more reaction chambers per row, fewer or more rows of waveguides, and may include other layout configurations. In some cases, there may be hundreds or even thousands of rows of waveguides. Optical power from the optical source 1-110 may be distributed to the multiple waveguides via one or more integrated star couplers or multi-mode interference couplers, or by any other means, located between an optical coupler to the chip 1-140 and the plurality of waveguides.

The inventors have discovered that in some cases problems can arise when trying to couple power from an optical source 1-110 efficiently to a large plurality of integrated optical waveguides 1-312. In order to provide sufficient power to each waveguide and reaction chamber 1-330 for a large number of reaction chambers, the average power in the input beam rises proportionally with the increase in number of reaction chambers. For some integrated optical waveguide systems (such as a silicon-nitride waveguide core/silicon-dioxide cladding), high average powers can cause temporal changes in the loss of the waveguide and therefore cause appreciable power instabilities in the reaction chambers over time. Time-dependent loss in integrated optical waveguides at high average powers has been measured by the inventors, and example results are plotted in FIG. 1-4. If average power levels from the laser become too high, optical damage may occur to integrated waveguides or other integrated optical components on the chip, particularly near where light couples into the chip.

Insertion loss was measured as a function of time for three identical lengths of, single-mode waveguides having a silicon-nitride core. The initial average power levels coupled into the three waveguides was 0.5 mW, 1 mW, and 2 mW. The plot of FIG. 1-4 shows the change in measured insertion loss for each length of waveguide as a function of time for the three power levels. The plot shows that at high power levels the loss can change by 3 dB in less than ten minutes. For some applications, such as single-molecule genetic sequencing where reactions may be run for tens of minutes or hours, such power instabilities may not be acceptable.

Further details of an embodiment of a hi-tech system 1-160 are described in connection with FIG. 1-5, which illustrates a portion of a bio-optoelectronic chip 1-140 that may be inserted into the hi-tech system 1-160 for massively parallel sample analysis. A non-limiting example of a biological reaction taking place in a reaction chamber 1-330 is depicted in FIG. 1-5. In this example, sequential incorporation of nucleotides or nucleotide analogs into a growing strand that is complementary to a target nucleic acid is taking place in the reaction chamber. The sequential incorporation of the nucleotides or nucleotide analogs can be detected to sequence DNA. The reaction chamber may have a depth between about 150 nm and about 250 nm and a diameter between about 80 nm and about 160 nm. A metallization layer 1-540 (e.g., a metallization for an electrical reference potential) may be patterned above the photodetector to provide an aperture that blocks stray light from adjacent reaction chambers and other unwanted light sources. According to some embodiments, polymerase 1-520 may be located within the reaction chamber 1-330 (e.g., attached to a base of the chamber). The polymerase may take up a target nucleic acid 1-510 (e.g., a portion of nucleic acid derived from DNA), and sequence a growing strand of complementary nucleic acid to produce a growing strand of DNA 1-512. Nucleotides or nucleotide analogs labeled with different fluorophores may be dispersed in a solution above and within the reaction chamber.

When a labeled nucleotide or nucleotide analog 1-610 is incorporated into a growing strand of complementary nucleic acid, as depicted in FIG. 1-6, one or more attached fluorophores 1-630 may be repeatedly excited by pulses of optical energy coupled into the reaction chamber 1-330 from the waveguide 1-315. In some embodiments, the fluorophore or fluorophores 1-630 may be attached to one or more nucleotides or nucleotide analogs 1-610 with any suitable linker 1-620. An incorporation event may last for a period of time up to about 100 ms. During this time, pulses of fluorescent emission resulting from excitation of the fluorophore(s) may be detected with a time-binning photodetector 1-322. In some embodiments, there may be one or more additional integrated devices 1-323 at each pixel for signal handling (e.g., amplification, read-out, routing, etc.) According to some embodiments, each pixel may include a single or multilayer optical filter 1-530 that passes fluorescent emission and reduces transmission of radiation from the excitation pulse. Some implementations may not use the optical filter 1-530. By attaching fluorophores with different emission characteristics (e.g., fluorescent decay rates, intensity, fluorescent wavelength) to the different nucleotides (A,C,G,T), detecting and distinguishing the different emission characteristics while the strand of DNA 1-512 incorporates a nucleic acid and enables determination of the genetic sequence of the growing strand of DNA.

According to some embodiments, a hi-tech system 1-160 that is configured to analyze samples based on fluorescent emission characteristics may detect differences in fluorescent lifetimes and/or intensities between different fluorescent molecules, and/or differences between lifetimes and/or intensities of the same fluorescent molecules in different environments. By way of explanation, FIG. 1-7 plots two different fluorescent emission probability curves (A and B), which may be representative of fluorescent emission from two different fluorescent molecules, for example. With reference to curve A (dashed line), after being excited by a short or ultrashort optical pulse, a probability $p_A(t)$ of a fluorescent emission from a first molecule may decay with time, as depicted. In some cases, the decrease in the probability of a photon being emitted over time may be represented by an exponential decay function $p_A(t)=P_{Ao}e^{-t/\tau_A}$, where $P_{Ao}$ is an initial emission probability and $\tau_A$ is a temporal parameter associated with the first fluorescent molecule that characterizes the emission decay probability. $\tau_A$ may be referred to as the "fluorescence lifetime," "emission lifetime," or "lifetime" of the first fluorescent molecule. In some cases, the value of $\tau_A$ may be altered by a local environment of the fluorescent molecule. Other fluorescent molecules may have different emission characteristics than that shown in curve A. For example, another fluorescent molecule may have a decay profile that differs from a single exponential decay, and its lifetime may be characterized by a half-life value or some other metric.

A second fluorescent molecule may have a decay profile that is exponential, but has a measurably different lifetime $\tau_B$, as depicted for curve B in FIG. 1-7. In the example shown, the lifetime for the second fluorescent molecule of curve B is shorter than the lifetime for curve A, and the probability of emission is higher sooner after excitation of the second molecule than for curve A. Different fluorescent molecules may have lifetimes or half-life values ranging from about 0.1 ns to about 20 ns, in some embodiments.

The inventors have recognized and appreciated that differences in fluorescent emission lifetimes can be used to discern between the presence or absence of different fluorescent molecules and/or to discern between different environments or conditions to which a fluorescent molecule is subjected. In some cases, discerning fluorescent molecules based on lifetime (rather than emission wavelength, for example) can simplify aspects of a hi-tech instrument 1-100. As an example, wavelength-discriminating optics (such as wavelength filters, dedicated detectors for each wavelength, dedicated pulsed optical sources at different wavelengths, and/or diffractive optics) may be reduced in number or eliminated when discerning fluorescent molecules based on lifetime. In some cases, a single pulsed optical source operating at a single characteristic wavelength may be used to excite different fluorescent molecules that emit within a same wavelength region of the optical spectrum but have measurably different lifetimes. A hi-tech system that uses a single pulsed optical source, rather than multiple sources at different wavelengths, to excite and discern different fluorescent molecules emitting in a same wavelength region can be less complex to operate and maintain, more compact, and may be manufactured at lower cost.

Although hi-tech systems based on fluorescent lifetime analysis may have certain benefits, the amount of information obtained by a hi-tech system and/or detection accuracy may be increased by allowing for additional detection techniques. For example, some hi-tech systems 1-160 may additionally be configured to discern one or more properties of a sample based on fluorescent wavelength and/or fluorescent intensity.

Referring again to FIG. 1-7, according to some embodiments, different fluorescent lifetimes may be distinguished with a photodetector that is configured to time-bin fluorescent emission events following excitation of a fluorescent molecule. The time binning may occur during a single charge-accumulation cycle for the photodetector. A charge-accumulation cycle is an interval between read-out events during which photo-generated carriers are accumulated in bins of the time-binning photodetector. The concept of determining fluorescent lifetime by time-binning of emission events is introduced graphically in FIG. 1-8. At time $t_e$ just prior to $t_1$, a fluorescent molecule or ensemble of fluorescent molecules of a same type (e.g., the type corresponding to curve B of FIG. 1-7) is (are) excited by a short or ultrashort optical pulse. For a large ensemble of molecules, the intensity of emission may have a time profile similar to curve B, as depicted in FIG. 1-8.

For a single molecule or a small number of molecules, however, the emission of fluorescent photons occurs according to the statistics of curve B in FIG. 1-7, for this example. A time-binning photodetector 1-322 may accumulate carriers generated from emission events into discrete time bins (three indicated in FIG. 1-8) that are temporally resolved with respect to the excitation time of the fluorescent molecule(s). When a large number of emission events are summed (e.g., corresponding to the areas under the curve for bin 1, bin 2, bin 3, the resulting time bins (depicted in the inset) may approximate the decaying intensity curve shown in FIG. 1-8, and the binned signals can be used to distinguish between different fluorescent molecules or different environments in which a fluorescent molecule is located. Examples of a time-binning photodetector 1-322 are described in U.S. patent application Ser. No. 14/821,656, filed Aug. 7, 2015, titled "Integrated Device for Temporal Binning of Received Photons," which is incorporated herein by reference.

In cases where emission intensities from the reaction chambers are low or where characterization of a sample depends upon intensity values from the reaction chambers, it is beneficial that the power delivered to the reaction chambers remains stable over time. For example, if the power delivered to the reaction chambers decreases by 3 dB (see FIG. 1-4) due to time-dependent loss in the waveguides, then the number of fluorescent emission events may fall to a level that is below a noise floor of the instrument. In some cases, failure to distinguish photon signals from noise can adversely affect photon statistics used to distinguish fluorophore lifetimes. As a result, important analytic information can be lost, errors in analysis may occur (e.g., errors in genetic decoding), or a sequencing run may fail.

II. Coupling an Output Beam from and Optical Source to a Hi-tech System

The inventors have conceived of apparatus and methods for coupling an output beam from and optical source to a hi-tech system. The apparatus (referred to as a "beam-shaping and steering assembly") can be assembled at moderate cost using a single, low-profile chassis (e.g., less than 35 mm in height) that supports all optical and mechanical components for automating dynamic adjustments to multiple beam parameters. The beam-shaping and steering assembly may measure less than 140 mm on its longest side and have a thickness less than 35 mm, in some embodiments. Because of its compact size, the assembly may be mounted in a portable hi-tech instrument that includes an optical source 1-110 and a hi-tech system 1-160, such as the portable DNA sequencing instrument described above. Other applications include, but are not limited to, uses for plate readers, gel scanners, polymerase chain-reaction (PCR) machines, fluorescence sorters, and microarray assays.

Because of its ability to adjust multiple beam parameters, the beam-shaping and steering assembly 1-150 can relieve the optical source and hi-tech system of specialized components needed for beam shaping and steering. The beam-shaping and steering assembly 1-150 can also accommodate manufacturing and assembly variations in the optical source and hi-tech system, as well as reduce the sensitivity of beam coupling to environmental factors such as temperature changes and vibrations. In some embodiments, a beam-shaping and steering assembly can handle pulsed optical beams with average powers up to 2 Watts with pulse durations as short as 10 picoseconds. The assembly may also be used to address time-dependent waveguide loss in a hi-tech system, such as the genetic sequencing system described above.

One approach to reducing the effects of time-dependent waveguide loss is to reduce the length of integrated waveguides used on a chip. In some cases though, appreciable lengths of waveguides may be needed to route optical signals to the reaction chambers. Alternatively or additionally, the intensity of radiation coupled into the waveguides may be reduced. The inventors have recognized and appreciated that the time-dependent waveguide loss may be most problematic where a beam from an optical source 1-110 is coupled first into a single waveguide of an integrated optical circuit and then redistributed among many waveguides. At the coupling region, the intensity may be very high and cause rapid changes in waveguide loss.

Figures 1A, 2:
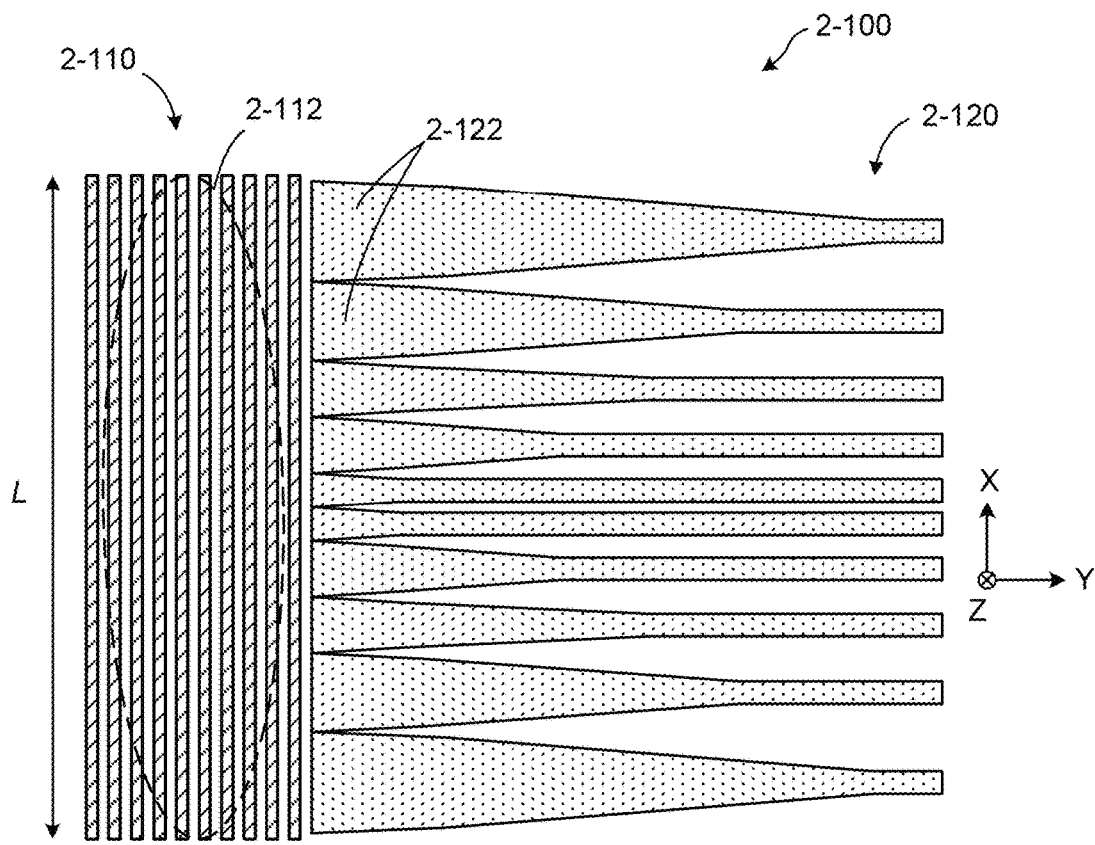

To reduce time-dependent waveguide loss at the coupling region, the inventors have conceived of a sliced grating coupler 2-100, of which a simplified illustration is shown in FIG. 2-1A. The sliced grating coupler may be a precision integrated optical component located on a chip in a hi-tech system 1-160, and comprise a grating 2-110 of length L formed adjacent to a plurality of waveguides 2-120. The waveguides may have tapered ends 2-122 that receive light diffracted by the grating 2-110. The tapered ends may have different widths (e.g., wider widths towards opposing ends of the grating, as depicted). The total width spanned by the tapered ends may be less than or approximately equal to the length L of the grating. The sliced grating coupler may be integrated onto a substrate that includes a photonic circuit and reaction chambers 1-330, for example.

In some embodiments, a beam from the optical source 1-110 may be shaped (or produced by the optical source) so that it extends in a ±X direction to essentially match an accepted large-area beam profile for a grating coupler having a length L. The large-area beam profile may have a beam length or first waist in the ±X direction (measured between $1/e^2$ intensity values) that approximately matches the length L for the grating and a beam width or second waist in the Y direction (measured between $1/e^2$ intensity values) that approximately matches a width of the grating. For example, the extended beam 2-112 may have a shape as depicted by the dashed ellipse in FIG. 2-1A. When such a beam is incident on the grating (e.g., travelling in the +Z direction), the grating will diffract the beam into the +Y direction towards the tapered ends 2-122 of the waveguides 2-120. The beam may have a transverse intensity profile in the X-direction that is most intense at its center and reduces in intensity moving toward the edges of the beam (reducing in the ±X directions). For such a beam, the tapered ends 2-122 of the waveguides may be wider at the opposing ends of the grating 2-110 and narrower at the center of the grating, so that similar amounts of power are coupled into each waveguide of the plurality of waveguides 2-120. Although 10 waveguides are shown in the drawing, a sliced grating coupler may have many more waveguides (e.g., between 20 and 2000). By distributing the coupling of power across many waveguides, adverse effects associated with time-dependent loss from initially coupling all the power into a single waveguide and subsequently distributing optical power into multiple waveguides can be reduced or eliminated. An expanded beam also reduces the intensity at the grating coupler and reduces the risk of damaging the grating 2-110 or the coupling region. In FIG. 2-1A and the other drawings, the coordinate axes are used merely for convenience in describing directions. Other orientations of the coordinate axes may be used without departing from the scope of the application.

The inventors have discovered that it is unexpectedly difficult to obtain a uniform coupling of power into the plurality of waveguides 2-120 with the sliced grating coupler 2-100 and beam arrangement depicted in FIG. 2-1A. Even though the transverse intensity profile of the beam may be Gaussian or well-characterized so that the different widths of the tapered ends 2-122 can be computed beforehand to theoretically capture equal amounts of power, the inventors found that the uniformity of coupling is highly sensitive to changes in the beam's transverse intensity profile and to beam displacement in the ±X directions.

Figures 1B, 2:
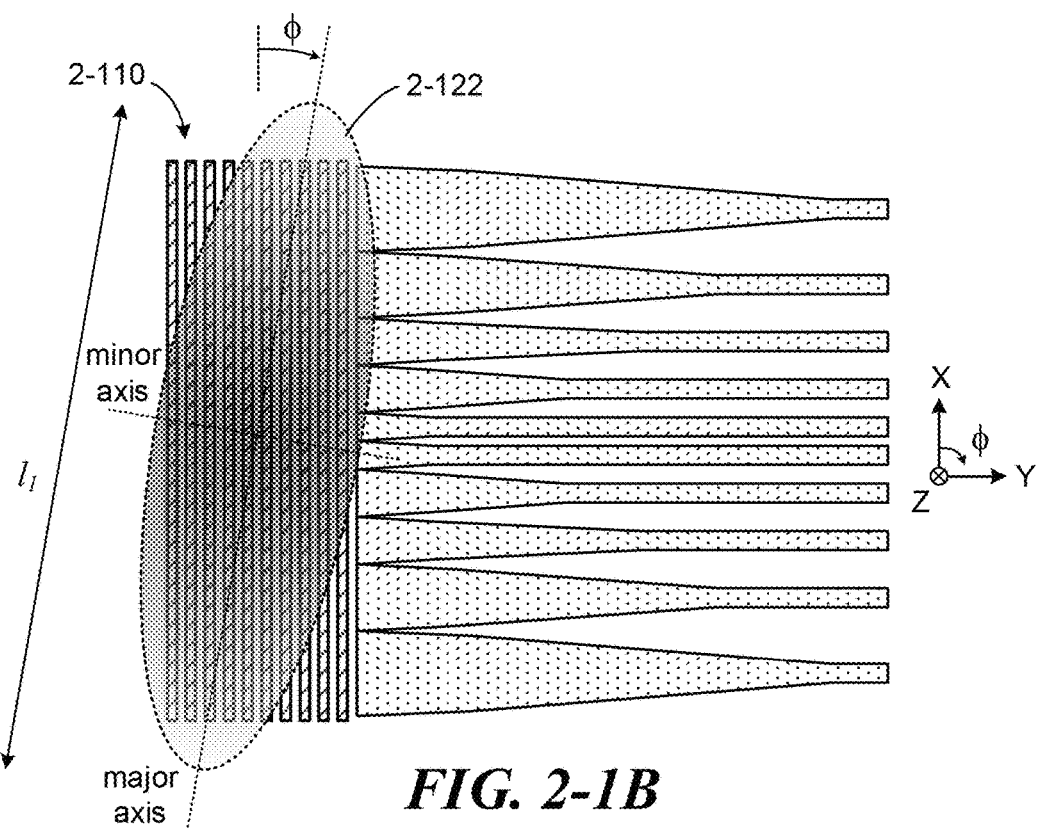

The inventors have conceived of an approach to coupling a wide beam to a plurality of waveguides that provides adjustments for improving uniformity of power levels coupled to the waveguides, reduces the sensitivity of coupling to the beam's transverse intensity profile and to beam displacement. The approach is illustrated in FIG. 2-1B. According to some embodiments, a round-shaped beam from an optical source (such as a laser) may be reshaped into an elliptical beam 2-122 that is oriented at an angle $\phi$ with respect to the grating lines. A length of the elliptical beam's major axis can exceed the length L of the grating 2-110 and array of tapered ends 2-122 and can be rotated such that the major axis of the ellipse is at a roll angle $\phi$ with respect to a longitudinal direction of the teeth or lines of the grating 2-110. The angle $\phi$ may be between 0.25 degree and 25 degrees in some embodiments. Portions of the beam 2-122 may extend beyond edges of the grating 2-110 in the ±X and ±Y directions. According to some embodiments, the beam-shaping and steering module 1-150 may reshape a round beam from an optical source 1-110 to an elliptical beam that is oversized between 10% and 35% compared to a length L that characterizes a length of a coupling region for the receiving grating 2-110 and adjacent tapered waveguide ends 2-122. As just one example, a round beam may be shaped into an ellipse having a major axis length $l_1$ of approximately 150 microns (measured between $1/e^2$ intensity values) for a coupling region of a grating 2-110 having a length L of approximately 120 microns. The length L of a coupling region for the grating 2-110 may be between 50 microns and 250 microns, and a width of the grating may be between 10 microns and 50 microns. Whereas the coupling arrangement shown in FIG. 2-1A may allow power from more than 95% of the beam area to couple into the tapered ends 2-122, the coupling arrangement shown in FIG. 2-1B may allow power from between 80% and 95% of the beam area to couple into the tapered ends, while also exhibiting decreased sensitivity to the length $l_1$ of the beam's major axis and improved power splitting uniformity across the waveguide array. The inventors have recognized and appreciated that a reduction in overall coupling efficiency is more than compensated by improvements in coupling stability, reduced sensitivity to beam length, and uniformity of coupled power into the waveguides. However, in some embodiments, the elongated beam may be aligned to the grating 2-110 or other receiving optical component with an angle that is approximately 0 degrees.

During operation, the roll angle $\phi$ and the beam displacement in the X and Y directions can be adjusted to obtain and maintain uniform coupling of power across the plurality of waveguides 2-120. To compensate for a beam 2-122 that has an asymmetric intensity profile in the X direction, the position of the beam may be adjusted in the ±X and/or ±Y directions to improve coupling uniformity across the waveguides 2-120. For example, if the intensity of the beam in the +X direction is greater than the intensity of the beam in the −X direction, then the beam may be moved in the −X direction to help equalize powers coupled into the waveguides. Additionally or alternatively, the beam may be moved in the +Y direction (for the angle shown) so that a portion of the beam in the +X direction moves in the +Y direction off the grating 2-110 and reduces the amount of power coupled to the tapered ends 2-122 in the +X direction while a portion of the beam in the −X direction moves onto the grating 2-110 and increases the amount of power coupled to the tapered ends 2-122 in the −X direction. If a beam 2-122 has a symmetric intensity profile in the X direction, then adjustments in the ±Y directions, ±X directions, and/or ±$\phi$ directions, for example, can be made to improve uniformity and/or efficiency of coupling power into the waveguides. In some implementations, adjustments to other beam parameters (e.g., incident angle, beam size, polarization) may be made additionally or alternatively to improve coupling efficiency and/or uniformity.

With regard to describing beam angles and directions, the +Z may is used to indicated the direction of travel of an optical beam. X and Y directions may be referred to as "transverse" or "lateral" directions. The X direction may be used to indicate a horizontal direction and the Y direction may be used to indicate a vertical direction. A rotation of the beam about the Z axis may be referred to as "roll" and indicated by the symbol $\phi$. A rotation about the X axis may be referred to as "pitch" and indicated by the symbol $\theta_x$. A rotation about the Y axis may be referred to as "yaw" and indicated by the symbol $\theta_y$.

Although adjustments to ±X and ±Y directions may be performed using actuated turning mirrors or optical windows, for example, adjustments to beam size and beam roll or rotation (±$\phi$) are not straightforward. For example, adjustments to beam size and beam rotation may couple to and affect other beam parameters, such as beam position. The inventors have also recognized and appreciated that adjustments to the beam's incident angle (pitch and yaw angles) on the grating without displacing the beam can be useful to improve coupling efficiency to the waveguides and to accommodate manufacturing variations in the optical source 1-110 and receiving optics of the hi-tech system 1-160. The inventors have further recognized and appreciated that a beam quality from the beam-shaping and steering assembly should be high (e.g., an $M^2$ value less than 1.5), so that efficient coupling can be achieved to optical components of a hi-tech system 1-160, in some cases. The inventors have appreciated that providing beam size, position, incident angle, and rotation adjustments with automated controls for multiple beam parameters along with a compact and stable assembly for in-field use is a difficult challenge.

Figures 2, 2A:
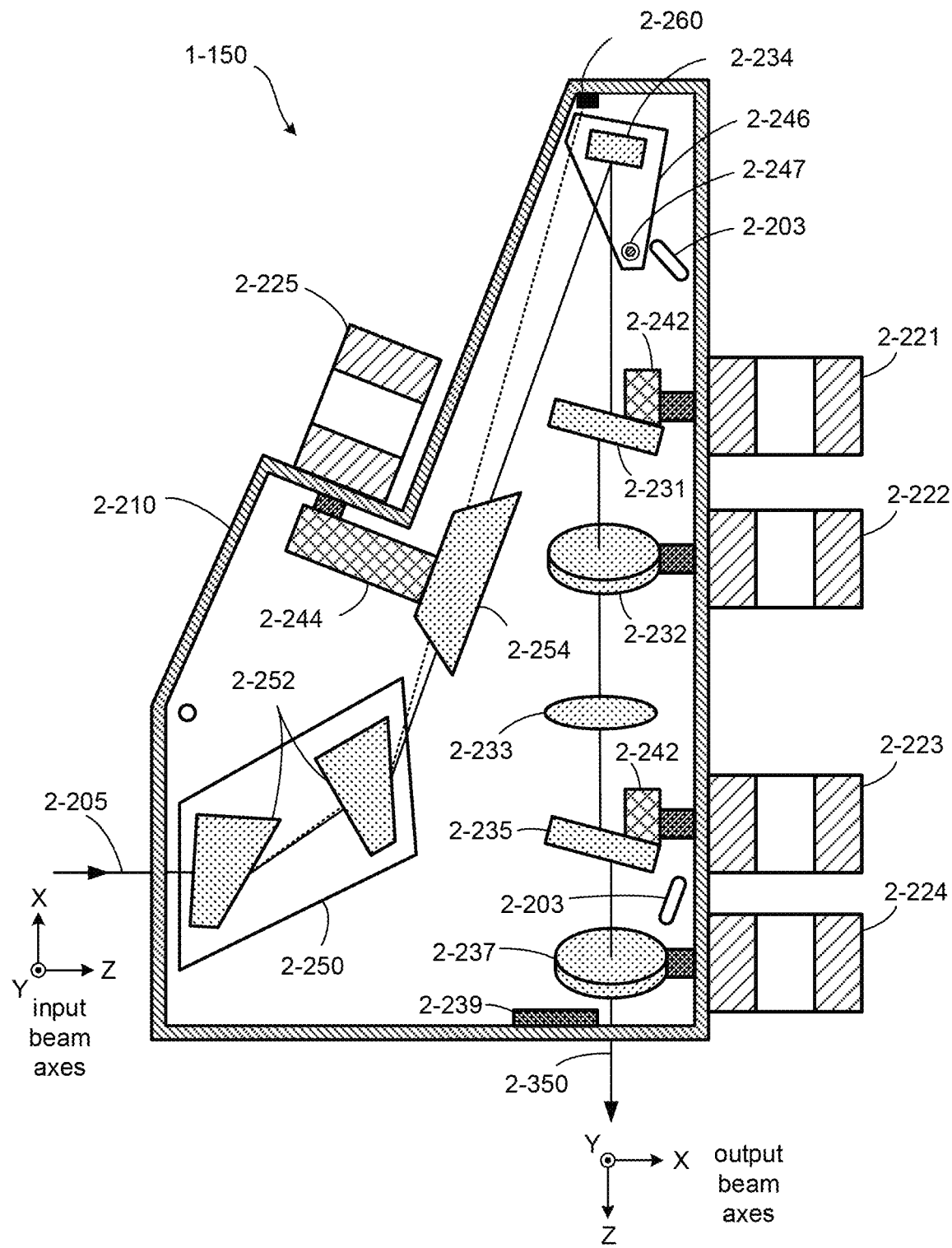

An example of a beam-shaping and steering module 1-150 is depicted in FIG. 2-2A. According to some embodiments, a beam-shaping and steering module may comprise a solid chassis 2-210 that is configured to support actuators and optical components of the beam-shaping and steering module. In embodiments, the chassis can include a base on which the optical components can be mounted, and may further include side walls, or a portion thereof, that can be attached to or integrally formed with the base. The module 1-150 can further include a cover that attaches to the chassis, so as to enclose the optical components. In some cases, the cover can include the side walls or a portion thereof.

The chassis and cover may be formed or assembled from metal and/or a low-thermal-expansion composite. In some cases, the chassis and cover may be machined or cast from a single piece of aluminum. When the chassis 2-210 is fabricated from a single piece of material, elements that hold optical components within the beam-shaping and steering assembly and/or the optical components themselves may be accurately aligned with respect to each other by registering the elements and/or components to alignment features machined into the chassis or alignment pins placed in the chassis. The chassis 2-210 may be in any suitable shape to house the optical components of the beam-shaping and steering module 1-150, and may be configured mount to a frame or chassis of an instrument in which the optical source 1-110 is incorporated.

Figures 2, 2B:
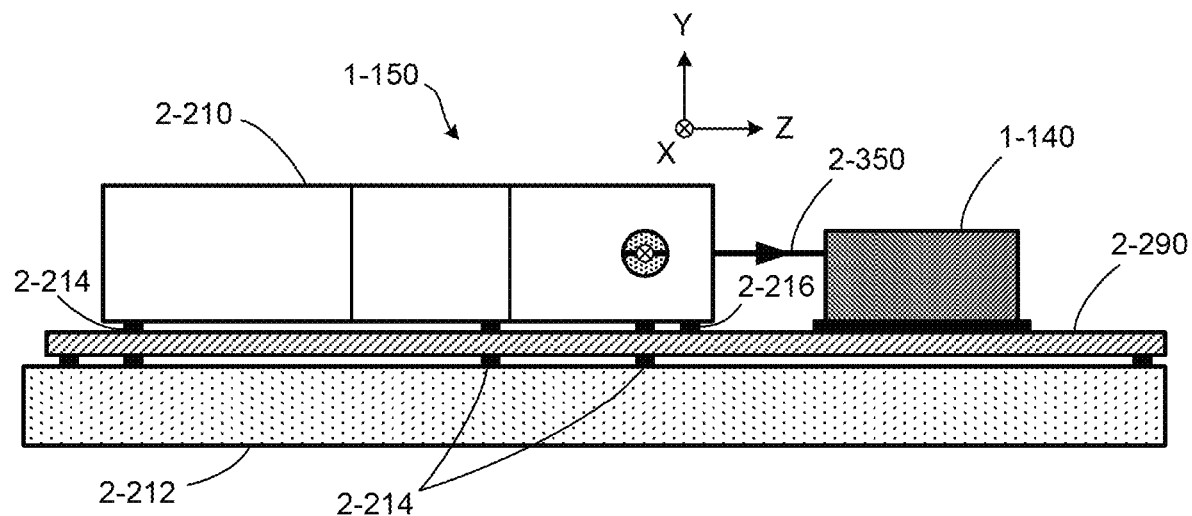
Figures 2, 3:
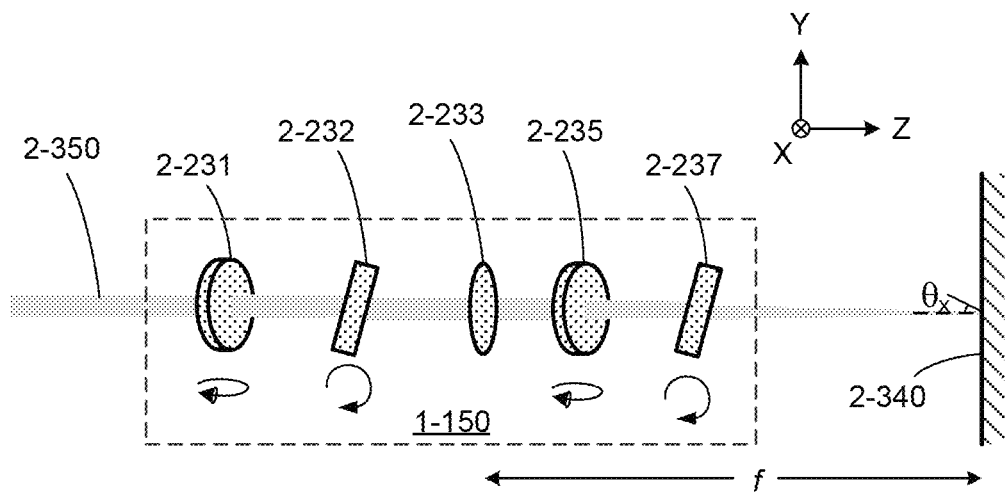
Figures 2, 3, 4:
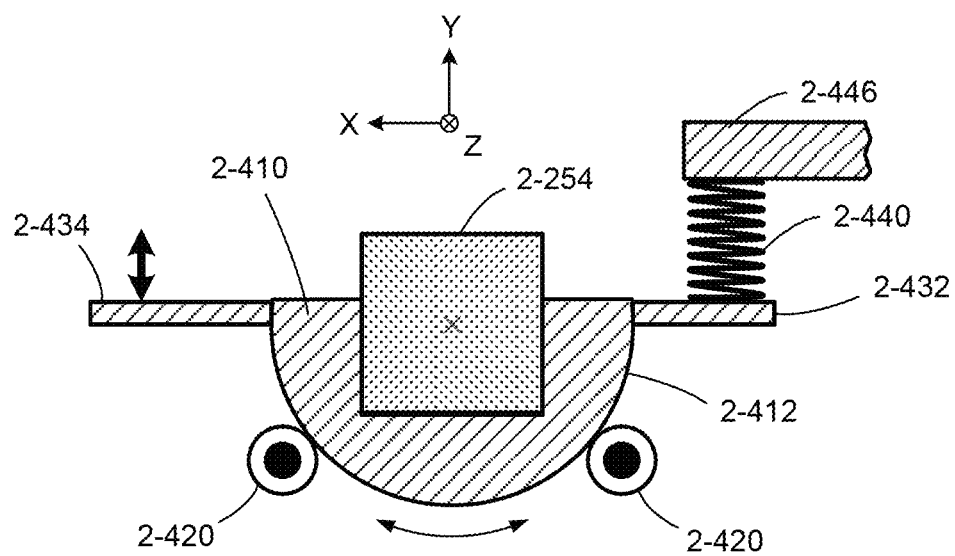
Figures 2, 3, 4, 5, 5A:
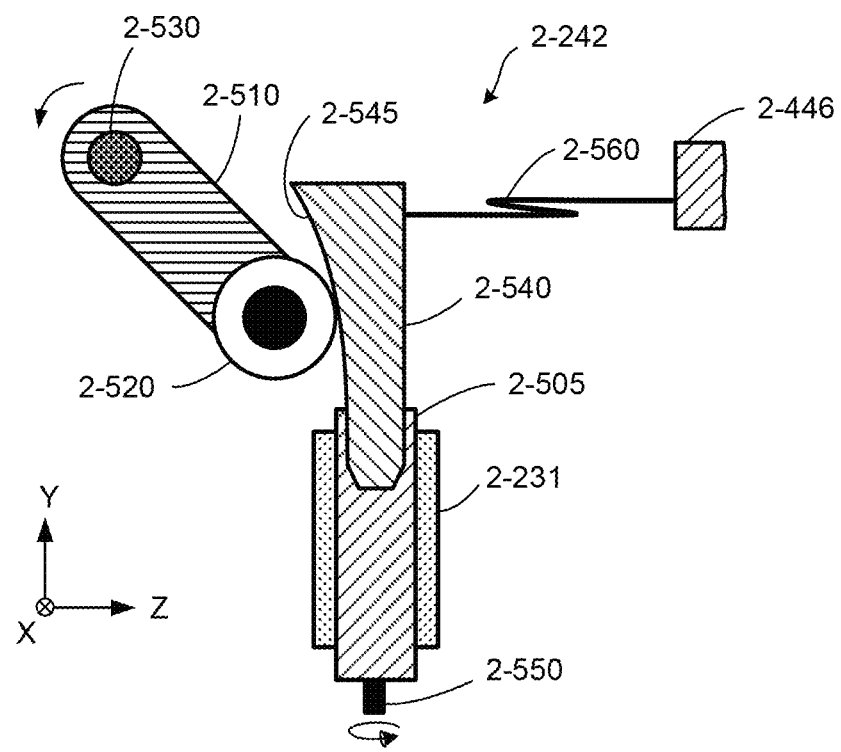
Figures 2, 3, 4, 5, 5B:
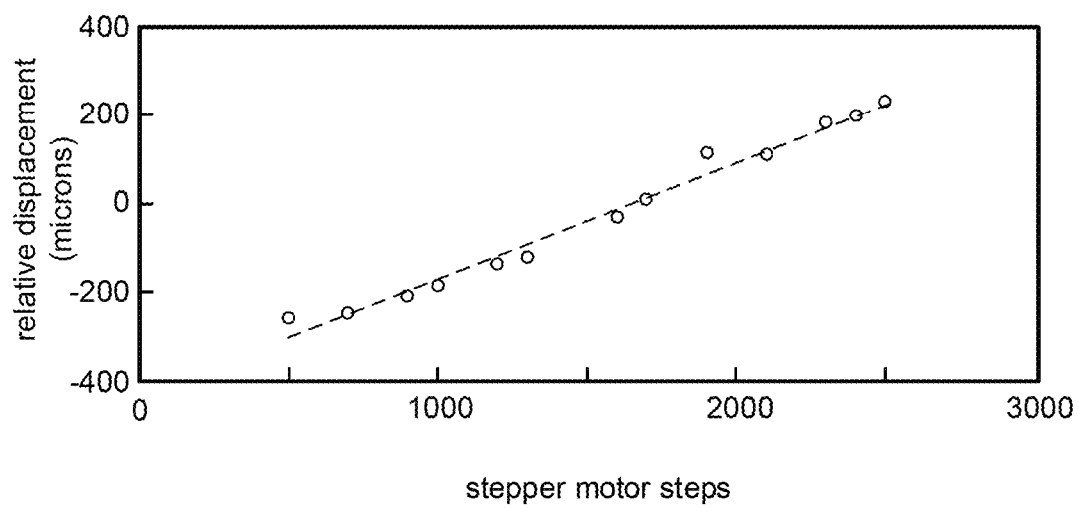
Figures 2, 3, 4, 5, 6:
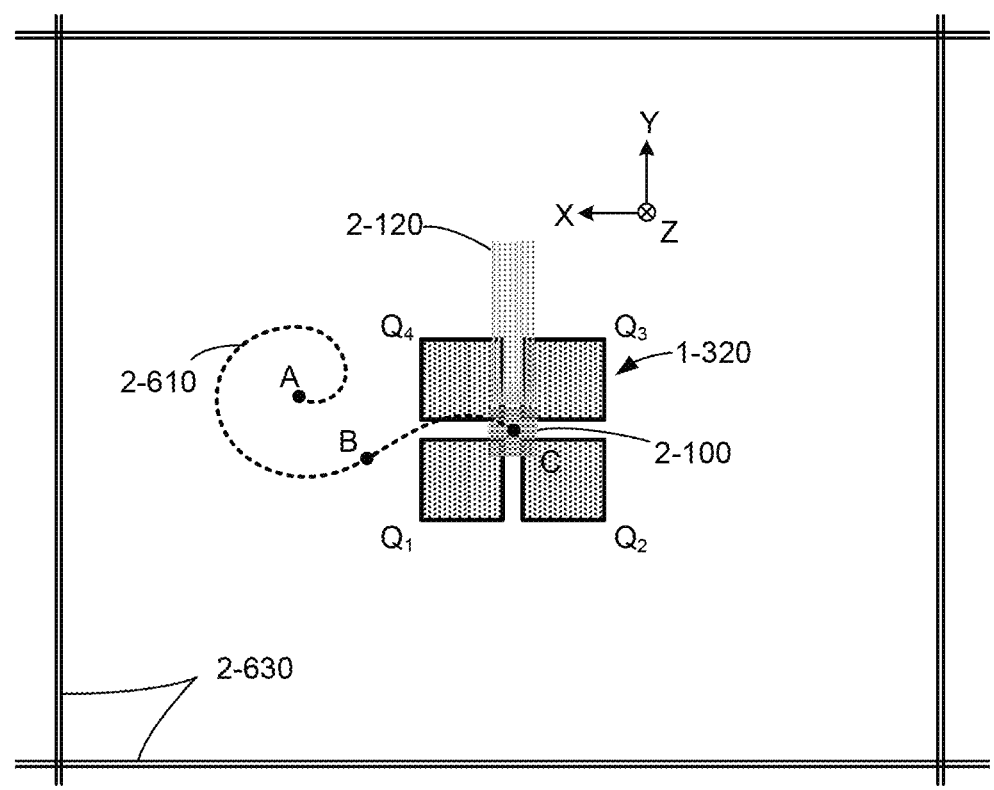
Figures 2, 3, 4, 5, 6, 7:
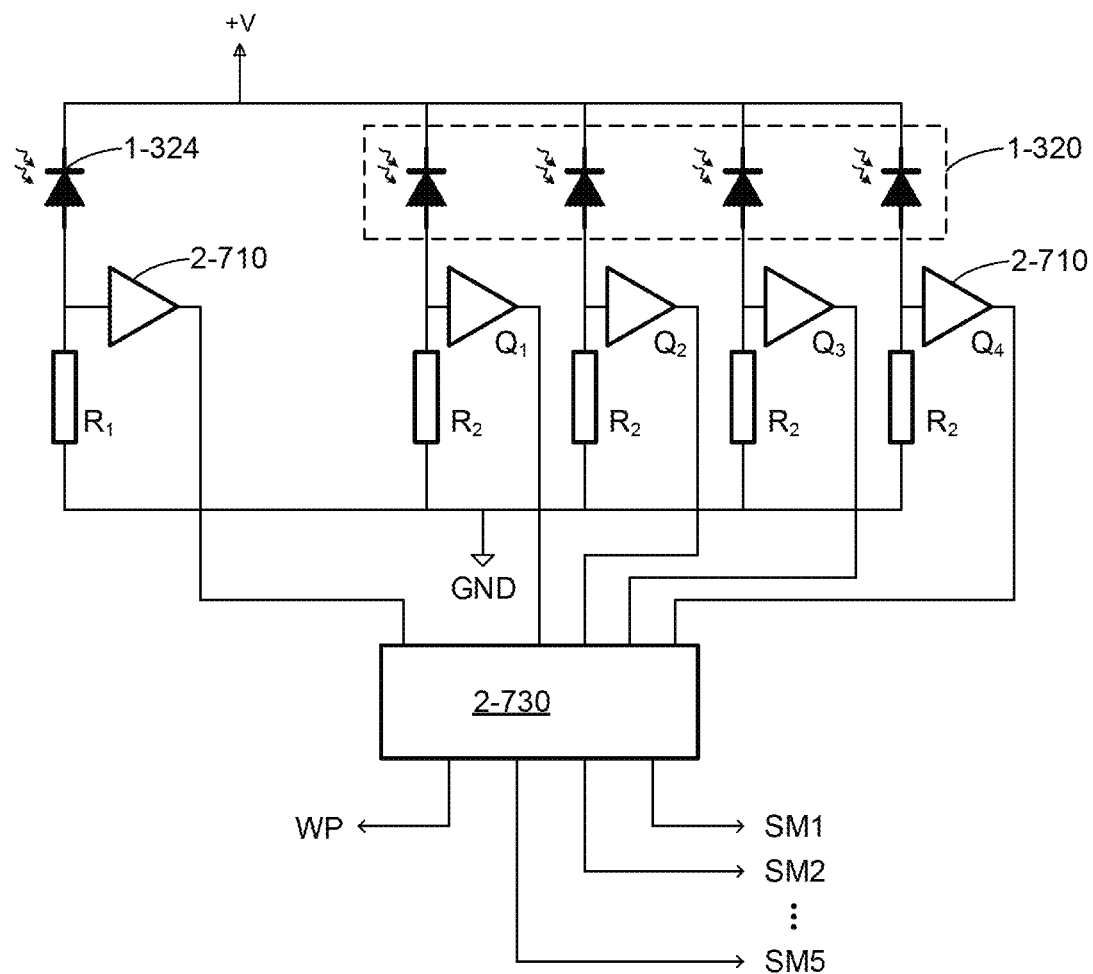

The inventors have recognized and appreciated that the beam-shaping and steering module's chassis 2-210 can additionally provide support to at least a region of a printed circuit board (PCB) 2-290 of a hi-tech system 1-160 on which a device with a receiving optical component, such as an analytic chip (e.g., a bio-optoelectronic chip 1-140), may be mounted as depicted in FIG. 2-2B. The beam-shaping and steering module's chassis 2-210 can stabilize an otherwise unsupported or moveable region of the PCB. For example, the chassis 2-210 may attach to a hi-tech instrument's chassis or frame 2-212 at several locations with mechanical mounts 2-214 (e.g., with height-adjusting screws) providing a rigid assembly that spans over an area of a PCB 2-290. A region of a PCB that supports an analytic chip 1-140 may be near the area spanned by the module's chassis 2-210 and can be secured to the beam-shaping and steering module's chassis 2-210 (e.g., with a fastener 2-216) to reduce relative motion (e.g., out-of-plane motion such as plate vibrations of the PCB from mechanical vibrations) between the beam-shaping and steering module 1-150 and the analytic chip 1-140. For example, a fastener 2-216 (e.g., a screw) can rigidly secure a region of the PCB 2-290 (which might otherwise be unsupported) to a location near an optical output port of the beam-shaping and steering module 1-150 and reduce or eliminate out-of-plane deflections of the PCB that might otherwise occur due to mechanical vibrations that couple to the PCB. Accordingly, the beam-shaping and steering module 1-150 can mechanically reduce vibrations that would otherwise act on and displace receiving optics of the chip or hi-tech system 1-160 with respect to the beam-shaping and steering module 1-150.

According to some embodiments, the chassis 2-210 and entire beam-steering assembly 1-150 can mount to an instrument's chassis or frame 2-212 such that the chassis' orientation can be adjusted with respect to the instrument's chassis or frame 2-212. For example, a three-point mounting scheme can be used where three mechanical mounts 2-214 each provide independent height adjustment of the chassis 2-210. By independently adjusting height with these mounts 2-214, one or more angles (e.g., pitch and roll angles) of the chassis 2-210 with respect to an input beam 2-205 can be adjusted in addition to overall height. In some cases, slots 2-203 (shown in FIG. 2-2A) formed at two mount locations (through which screws from the mechanical mounts can extend) could allow for further angle adjustment (e.g., yaw) of the chassis 2-210 with respect to the input beam 2-205.

In some embodiments, actuators of a beam-shaping and steering module 1-150 may comprise one or more stepper motors (five in the illustrated embodiment, 2-221, 2-222, 2-223, 2-224, 2-225) arranged to actuate optical components of the beam-shaping and steering module. To reduce height of the beam-shaping and steering module, the actuators may be mounted such that their shafts lie approximately in a same plane, as depicted in the drawing. In some implementations, one or more stepper motors may have shafts that are orthogonal to the plane or at other orientations. In some cases, one or more stepper motors may be fabricated in part on a PCB that can attach to the beam-shaping and steering module, as depicted in the example of FIG. 2-2B. For example, a stepper motor (not shown) fabricated on the PCB 2-290 can extend into the beam-shaping and steering module 1-150 and actuate an optical component to rotate about a Y axis. An example of a stepper motor fabricated in part from a PCB is described in U.S. provisional patent application 62/289,019, which is incorporated herein by reference.) A motor fabricated in part from a PCB may include a drive shaft configured to rotate an optical component of the beam-shaping and steering module about an axis that is perpendicular to the plane of the PCB. Other types of actuators (e.g., piezo-electric actuators, linear motors) may be used as actuators in some implementations.

According to some embodiments and referring again to FIG. 2-2A and an optical representation in FIG. 2-3, a beam-shaping and steering module 1-150 can include a first optical window 2-231, a second optical window 2-232, a focusing lens 2-233, a third optical window 2-235, and a fourth optical window 2-237. In some cases, optical flats with surfaces having a flatness as good as λ/20 or better can be used for higher beam quality instead of optical windows. For safety, an optical shutter 2-239 may be included in the assembly 1-150 to block an output beam. In embodiments, the transparent optical windows can be actuated by actuators (such as stepper motors 2-221, 2-222, 2-223, 2-224, respectively) to adjust beam position and beam incident angle at a focal point of the focusing lens 2-233. The optical windows and focusing lens may be anti-reflection coated to reduce unwanted Fresnel reflections from the optics. The opposing faces of the optical windows may be parallel to within 10 arc-seconds, according to some embodiments, though less parallelism can be tolerated in some cases. The optical windows may have a same thickness, or may have different thicknesses. The thickness of an optical window may be between 3 mm and 20 mm Although turning mirrors may be used in some cases to adjust beam position and incident angle, an advantage of optical windows is that they are substantially immune, to first order, from coupling mechanical vibrations from the chassis 2-210 into changes in beam position and incident angle. For example, even though and optical window may be displaced by vibrational motion, the optical beam path of a beam passing through the optical window should remain unchanged. Additionally, thermal expansion effects or manufacturing variations in optical mounts for the optical windows that might displace the optical windows would not affect the beam path to first order. In some implementations, there may be one or more turning mirrors 2-234 located within the beam-shaping and steering module to redirect the beam path, though in some cases a beam path through a beam-shaping and steering module may be straight or curved and no turning mirror may be used to fold the beam path.

According to some implementations, the turning mirror 2-234 may be dichroic, such that it passes one or more wavelengths in a first wavelength range, and reflects one or more wavelengths in a second wavelength range. For example, a dichroic-coated turning mirror 2-234 may pass a fundamental wavelength in the infrared wavelength region from an optical source 1-110 to a beam dump and/or photodetector (not shown) and reflect a frequency-doubled wavelength in the visible spectral range to a bio-optoelectronic chip 1-140. In other implementations, the turning mirror 2-234 may have a reflective coating for a single characteristic wavelength, and not be dichroic. In such implementations, separation of wavelengths in the input beam may be achieved with other optical components (e.g., interference filter, pellicle, prism) in the beam-shaping and steering assembly.

In embodiments, a turning mirror 2-234 can be mounted on an adjustable mount 2-246, which can be adjusted by a set screw 2-247, for example. Such an adjustment may be in only one degree of freedom. For example, adjusting set screw 2-247 can coarsely adjust an elevation angular direction of the beam 2-350 through the optical windows 2-231, 2-232, 2-235, 2-237 and lens 2-233. In some cases, turning mirror 2-234 can be mounted to the chassis 2-210 with a non-adjustable mounting arrangement.

According to some embodiments and referring to both FIG. 2-2A and FIG. 2-3, the first optical window 2-231 may be rotated by the first actuator 2-221 about a first axis of rotation. To aid explanation, a right-hand, orthogonal coordinate system XYZ, with the +Z axis pointing in the direction of beam travel, is indicated in the drawings for the outgoing beam 2-350. The first axis of rotation may be essentially parallel to a Y axis to shift an incoming optical beam 2-350 in the ±X directions immediately after the first optical window. The second optical window 2-232 may be rotated by the second actuator 2-222 about a second axis of rotation that is essentially perpendicular to the first axis of rotation to shift the optical beam in the ±Y directions immediately after the second optical window. In some implementations, the order of the first and second optical windows may be reversed. The third optical window 2-235 may be rotated by the third actuator 2-223 about a third axis of rotation that is essentially parallel to the first axis of rotation to shift the optical beam in the ±X directions immediately after the third optical window. The fourth optical window 2-237 may be rotated by the fourth actuator 2-224 about a fourth axis of rotation that is essentially perpendicular to the first axis of rotation to shift the optical beam in the ±Y directions immediately after the fourth optical window. In some implementations, the order of the third and fourth optical windows may be reversed.

The effects on a focused optical beam at a substrate surface 2-340 due to translating the optical beam 2-350 in the beam-shaping and steering module 1-150 can be understood from FIG. 2-3. The surface of the substrate may be located at, or approximately at, a focal point of the focusing lens 2-233. For example, the outgoing optical beam 2-350 may pass through the focusing lens 2-233 and be focused onto a sliced grating coupler 2-100 at a bio-optoelectronic or other analytic chip 1-140. Lateral translations of the optical beam 2-350 by rotating optics located after the focusing lens 2-233 results in ±X, ±Y translations at the surface 2-340. As an example, rotation of the third optical window 2-235 about its axis of rotation may translate the focused beam at the surface 2-340 in a direction parallel to the X axis by as much as ±1200 microns when the optical window 2-235 has a thickness of approximately 6 mm and a refractive index of approximately 1.5. Rotation of the fourth optical window 2-237 about its axis of rotation may translate the focused beam at the surface 2-340 in a direction parallel to the Y axis by as much as ±1200 microns when the optical window 2-237 has a thickness of approximately 6 mm and a refractive index of approximately 1.5. Less or more motion of the beam may be achieved for thinner or thicker optical windows, respectively. Additionally, an optical window having a material with a high refractive index (e.g., greater than approximately 1.5) may provide larger beam displacements.

Lateral translations of the optical beam 2-350 by rotating optics 2-231, 2-232 located before the focusing lens 2-233 results in changing the incident angles (pitch and yaw angles) of the focused beam at the surface 2-340 without appreciably changing the beam's (X, Y) location at the surface 2-340. For example, rotation of the first optical window 2-231 about its axis of rotation can displace the optical beam in the ±X directions at the focusing lens 2-233. Such movement of the optical beam at the focusing lens will change an incident angle $\theta_y$ or yaw (not shown in FIG. 2-3) of the optical beam with respect to the Z axis in the XZ plane at the surface 2-340 by as much as ±1.0 degree, when the optical window has a thickness of approximately 9 mm and a refractive index of approximately 1.8. In some embodiments, rotation of a second optical window 2-232 about its axis of rotation displaces the optical beam in the ±Y directions and causes a change in incident angle $\theta_x$ or pitch in the YZ plane at the surface 2-340 by as much as ±1.0 degrees. Because the surface 2-340 is located at approximately the focal distance f of the lens 2-233, changes in incident angle by as much as ±1.0 degree by translating the beam 2-350 before the lens will not appreciably affect the (X, Y) location of the focused beam at the surface 2-340. In some cases, the resulting cross-coupling lateral displacement in X and Y of a beam's position at a target location (e.g., at surface 2-340) is at most ±10 microns. In some cases the cross-coupling lateral displacement at the target location, due to rotation of optical windows 2-231, 2-232 can be no greater than ±5 microns. Larger changes in incident angle (e.g., as high as ±10 degrees) can be obtained when the lens 2-233 has a shorter focal length and thicker optical windows are used, though the cross-coupling displacement may not change.

By automating motion of one or more of the optical windows 2-231, 2-232, 2-235, 2-237, continuous scanning of the output beam may be performed in one or multiple degrees of freedom. For the embodiment depicted in FIG. 2-2A, continuous scanning for the second optical window 2-232 and fourth optical window 2-237 may be implemented by rotating the optical windows continuously in a same direction. Continuous scanning modes may be useful for aligning the output beam to a receiving optical component or port in a hi-tech system 1-160. Continuous or step-wise scanning may also be useful for coupling the output beam to multiple receiving optical components or ports in a hi-tech system. For example, the output beam may be stepped sequentially to different grating couplers on a same chip or on different chips in a hi-tech system 1-160. In this manner, multiple different assays (each having a plurality of sample wells for sample analysis) may be performed nearly simultaneously.

In some embodiments, there may be a turning mirror (not shown in FIG. 2-3) located between the surface 2-340 and the beam-shaping and steering module 1-150 to deflect the beam in the −Y direction or +Y direction, so that the surface 2-340 may be parallel to the incoming optical beam 2-350. This would allow a bio-optoelectronic chip 1-140, for example, to be mounted parallel to an underlying printed circuit board, as depicted in FIG. 2-2B. In some cases, the turning mirror may be formed at low cost from a small portion (e.g., less than 5 mm square) of a silicon wafer, fused silica, or other polished substrate, coated with a reflective material, and mounted within a package containing the bio-optoelectronic chip 1-140.

In some implementations, the focusing lens 2-233 may be a singlet lens having a focal length between 5 centimeters and 1 meter. Alternatively, the focusing lens 2-233 may be one of a pair of relay lenses, where the other lens may be located inside or outside of the beam-shaping and steering assembly 1-150. In some embodiments, lens 2-233 may be a zoom lens. The position, magnification, and/or demagnification of the focusing lens 2-233 may be controlled manually (e.g., by a user operating a positioner (not shown) on which the lens is mounted) or may be controlled automatically via an actuator so that dynamic adjustments may be made to the lens' position, magnification, and/or demagnification. In some implementations, the lens 2-233 may be installed in a fixed lens mount that is positioned at the time of manufacture or positioned by a user.

Adjustments to beam shape and beam rotation can be achieved with optical prisms, according to some embodiments. In some implementations, an anamorphic prism pair 2-252 may be used to compress or expand one dimension of an input optical beam's transverse intensity profile. With reference to FIG. 2-2A, the anamorphic prism pair may compress the transverse intensity profile of the input optical beam 2-205 in one direction (X direction referenced to the incoming optical beam 2-205) by a factor between 3 and 8 (depending upon the prism shapes), and not affect the Y-directed transverse intensity profile. The amount of compression or expansion may be determined by cut angles between the prism entrance and exit faces through which the optical beam passes. According to some implementations, the prisms may be cut with an angle between 15 degrees and 45 degrees between the entrance and exit prism faces. The prism faces may be coated with an anti-reflective coating. Because of the compression in one dimension (the X dimension in the example shown), the optical beam's width in the X direction at the focus of lens 2-233 will be larger or extended compared to the Y-directed transverse intensity profile, as indicated in FIG. 2-1B. In some embodiments, adjustments to beam size and ellipticity may be made by moving the focusing lens 2-233 along the optical beam path (e.g., moving lens 2-233 with a linear actuator) and/or changing an effective magnification or demagnification provided by the focusing lens 2-233 (e.g., changing a zoom lens setting).

Although a pair of cylindrical lenses may be used in some implementations to expand or compress an optical beam, the inventors found that the resulting beam shape is highly sensitive to alignment of the lens pair. For example, if the cylindrical lens pair is rotated about the optical axis of the beam by an amount as small as 1 degree, then the resulting beam shape rotates by more than five times this amount.

According to some embodiments, the anamorphic prism pair 2-252 may be aligned at the time of manufacture. For example, the prisms may register to machined aligning features and/or pins (not shown) formed or mounted in the chassis 2-210. In some implementations, the prisms may register to machined features and/or pins formed or mounted in an intermediate plate 2-250 that can register to aligning features on the chassis 2-210 and be attached to the chassis 2-210. In some cases, the orientation of the intermediate plate 2-250 may be adjustable within the chassis for fine tuning of the prism pair (e.g., for factory alignment). In some cases, each prism of the anamorphic prism pair 2-252 may be individually adjustable (e.g., mounted on a rotary positioner). Additionally or alternatively, the intermediate plate 2-250 could include a rotational adjustment or be mounted on a rotary positioner. The orientation of the prism pair, or each individual prism of the pair, may be automated with one or two stepper motors in some embodiments. The inventors have recognized and appreciated that the anamorphic prism pair can be adjusted manually at time of manufacture to flexibly adapt a beam shape from an optical source to a hi-tech system for a suitably wide variety of beam shapes, and quality of coupling to the hi-tech system can be handled dynamically with automated beam rotation, displacement, and incident angle adjustments provided by other optical components in the beam-shaping and steering assembly 1-150.

An anamorphic prism pair 2-252 can provide additional benefits to the beam-shaping and steering assembly 1-150. A first benefit is that it can provide spatial separation of optical beams at different wavelengths. In some implementations, an input beam 2-205 to the assembly may comprise multiple frequencies (e.g., a fundamental frequency or wavelength from a laser and a second harmonic frequency or frequency-doubled wavelength output from a nonlinear optical element in the laser beam path). The anamorphic prism pair 2-252 can refract the two different wavelengths in different directions, as depicted by the dashed and solid lines in FIG. 2-2A. For example, an infrared portion of the incoming optical beam 2-205 may travel along the dotted-line path to a beam dump 2-260 and/or photodiode, for example, and a frequency-doubled portion of the optical beam 2-205 may travel along the solid-line path through the assembly 1-150. A second benefit of the anamorphic prism pair 2-252 is that it can reduce a sensitivity of beam coupling to ±X displacements of the input beam 2-205. The reduction in sensitivity is due to a demagnification of the optical beam by the prism pair in the X direction.

Additionally, the beam shape is unaffected by the position of the input beam in the X and Y directions, provided the beam is not clipped by an edge of either prism in the prism pair 2-252. In this regard, the beam shape has reduced sensitivity to vibration, thermal expansion, and/or machining variations that would displace the prism pair relative to the input beam. For example, the incoming optical beam 2-205 may displace up to ±3 mm in the X or Y directions without affecting the elliptical beam shape after the prism pair 2-252. Immunity of beam shape to X and Y displacements is not possible when a crossed pair of cylindrical lenses is used in the assembly 1-150 to reshape the input beam 2-205.

Other implementations relating to beam shaping may be employed. According to some implementations, the anamorphic prism pair 2-252 may be used or arranged in reverse, such that it can transform an elliptical beam into a round beam. This may be useful for converting a transverse beam profile from a diode laser from an elongated shape to a more round shape, for example. In some embodiments, conversion of beam shape may not be required so that an anamorphic prism pair 2-252 is not used, and one or more turning mirrors may be installed in place of the anamorphic prism pair 2-252. In such embodiments the image rotation prism 2-254 may be used to rotate polarization of the input beam. In some cases, a Galilean beam expander may be used instead of the anamorphic prism pair to resize (magnify or demagnify) an input beam of any shape. According to some embodiments, one or more polarization rotators (half-wave plate) or transformer (quarter wave plate, polarizing film) may be installed in the beam-shaping and steering assembly at any suitable location to operate on polarization of the input beam. A polarization rotator or polarization transformer may be rotated manually (by a user) or automatically (by an actuator).

Rotation of the transverse beam shape and polarization can be achieved using an image rotation prism 2-254, according to some embodiments. In some embodiments, a beam exiting the anamorphic prism pair 2-252 may pass centrally through the rotation prism that is rotated about an axis of rotation that is approximately parallel to the optical axis of an optical beam entering the prism. Rotation of the prism can rotate the optical beam's transverse shape and its polarization about its optical axis exiting the prism. In this manner, an optical beam with an elliptical transverse beam shape (as depicted in FIG. 2-1B) can be rotated about its optical axis (e.g., in the ±ϕ direction illustrated in FIG. 2-1B). According to some embodiments, the rotation prism may be a dove prism. Other embodiments with different optical layouts may use other image rotation prisms (e.g. a Schmitt prism, a group of mirrors).

Figures 1, 2, 3, 4:
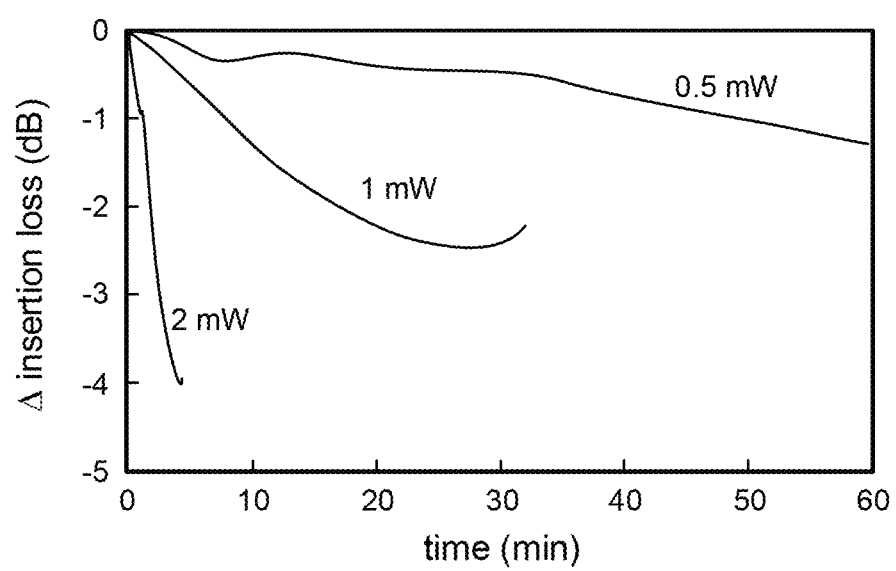
Figures 1, 2, 3, 4, 5:
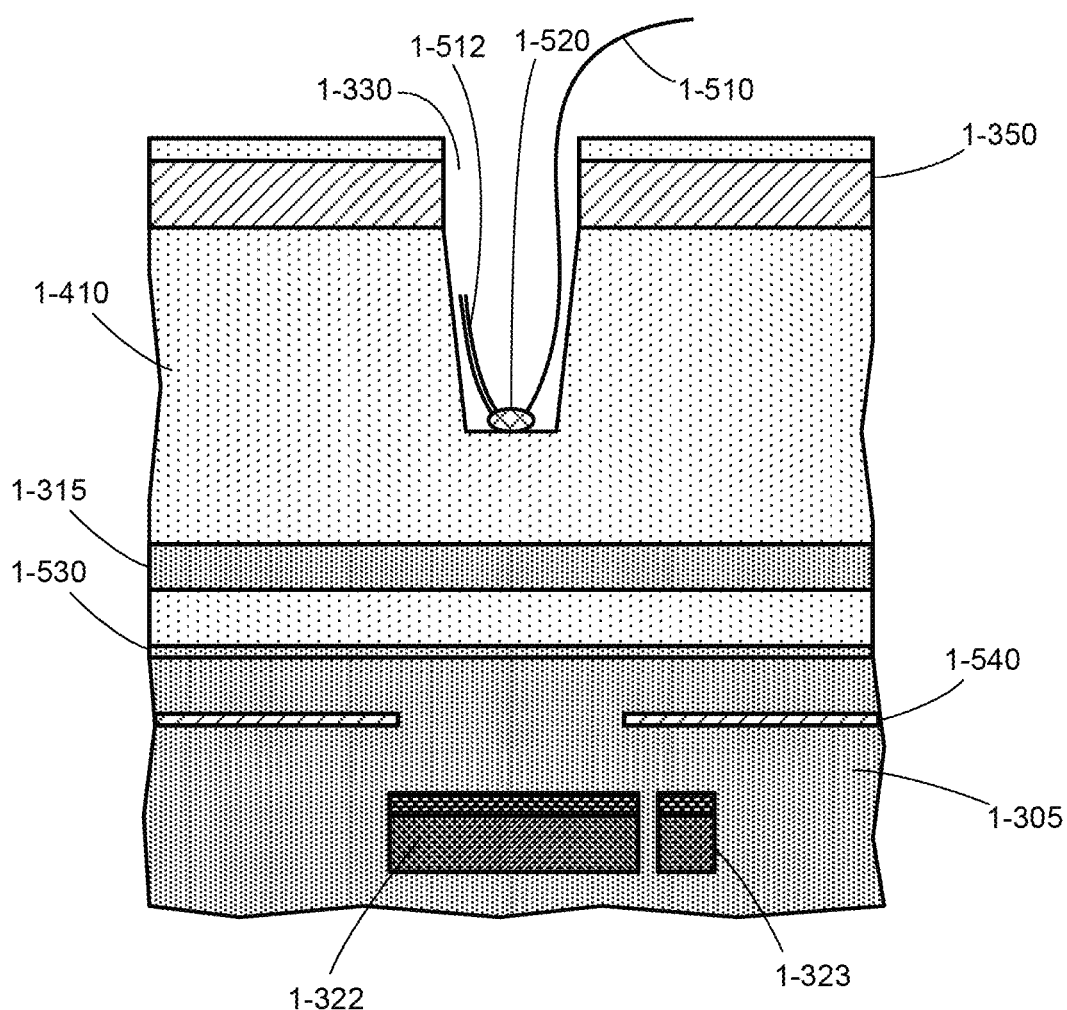
Figures 1, 2, 3, 4, 5, 6:
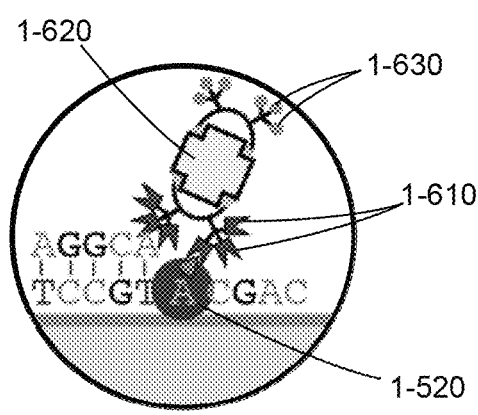
Figures 1, 2, 3, 4, 5, 6, 7:
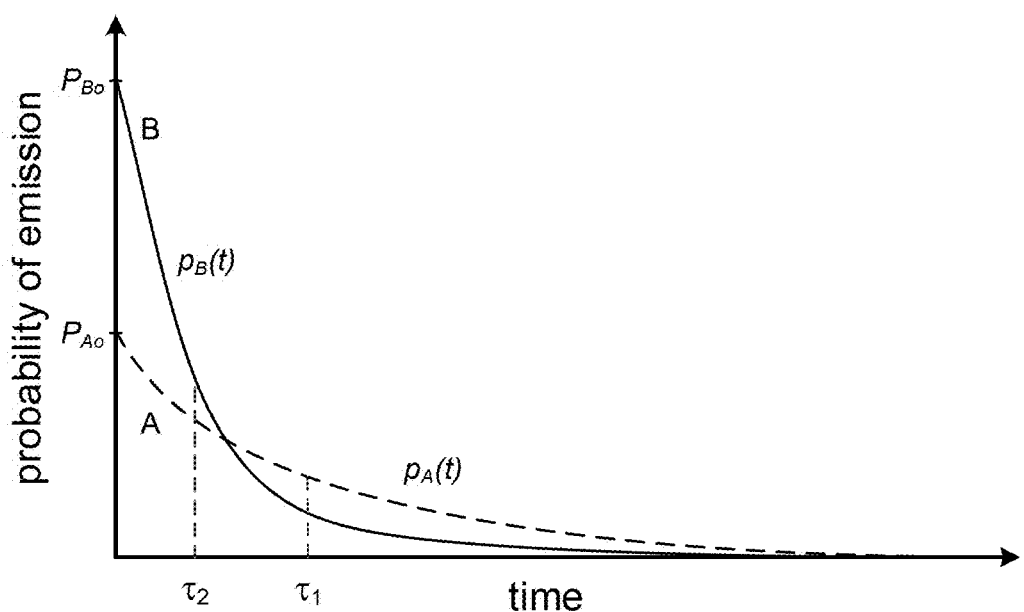
Figures 1, 2, 3, 4, 5, 6, 7, 8:
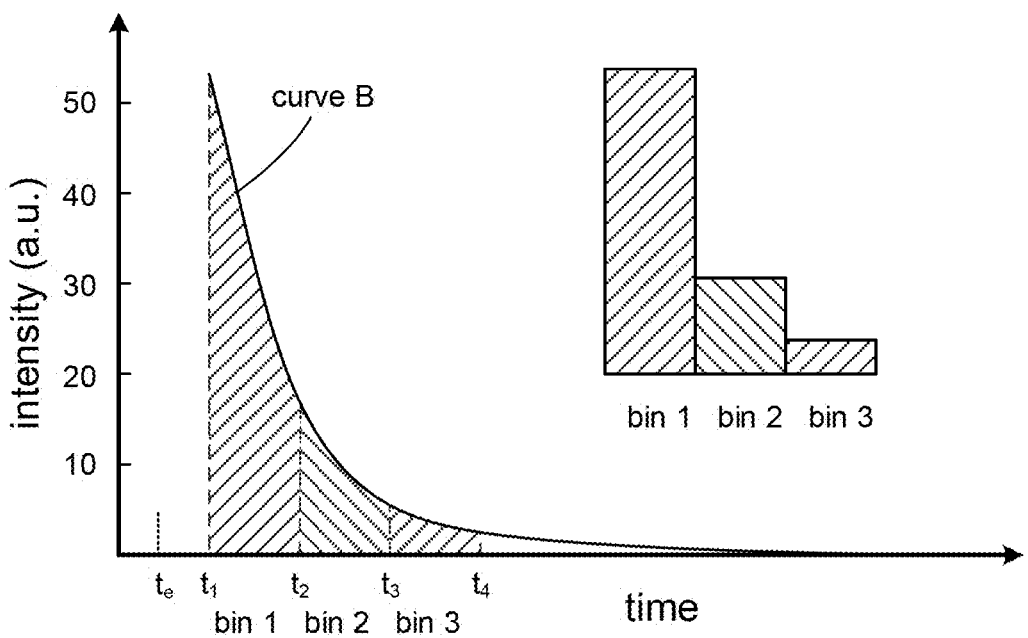

In some implementations, an image rotation prism 2-254 can be mounted in a rotation assembly having a cradle 2-410 that rotates about an axis of rotation, which is parallel to the optical beam's Z axis in the illustration of FIG. 2-4. The cradle may have a cylindrical surface 2-412 that rides on at least three bearings 2-420, according to some embodiments. In some cases, four bearings 2-420 can be used. The bearings may be mounted on rods or axles that are mounted to the chassis 2-210. An actuator (e.g., stepper motor) may press and release on a lever arm 2-434 to rotate the cradle. In some embodiments, a compression spring 2-440 (or any other suitable spring) backed by a support 2-446 can act on a counter-lever arm 2-432 to provide stabilizing counterbalancing force against the actuator pressing on lever arm 2-434, remove any backlash in mechanical linkage, and to retain the cradle against the bearings 2-420. In some cases, the support 2-446 can comprise a portion of a cover mounted over the beam-shaping and steering assembly 1-150. With a stepper motor pressing on the lever arm 2-434, the cradle 2-410 may be rotated by ±12.5 degrees. Due to the optical reflection through the prism, the beam shape may be rotated at the surface 2-340 as much as ±25 degrees. The resolution of beam rotation may be less than 0.1 degree per step of a stepper motor (e.g., between 0.01 degree/microstep and 0.1 degree/microstep) using commercially-available stepper motors.

The cradle 2-410 may include a machined recess in which the image rotation prism 2-254 may be mounted, so that a center of rotation of the image rotation prism is concentric with the axis of rotation of the cradle. The machined recess may comprise one or more alignment faces or pins that are aligned to be approximately parallel to a planned optical beam path in the beam-shaping and steering assembly 1-150 when assembled. During assembly, the image-rotation prism 2-254 may be aligned by registering the prism to one or more of the alignment faces or pins and securing the prism in the cradle with any suitable fastening means. Additionally, rods that support the bearings 2-420 may be aligned in parallel to machined features in the chassis 2-210, so that a central axis of the rotation prism approximately coincides with an axis of rotation of the cradle 2-410 and with a planned optical beam path through the beam-shaping and steering assembly 1-150. Accordingly, an input beam 2-205 aligned approximately to a planned optical beam path through the assembly will have its shape (transverse intensity profile) rotated with minimal change in beam displacement and beam direction.

The inventors have also recognized and appreciated that it is beneficial to have a low-profile shape of the beam-shaping and steering assembly 1-150. This can be difficult when the same type of actuator (e.g., a rotary stepper motor) is used to operate on all moveable optical components within the assembly. Use of a same type of actuator can be beneficial in terms of reduced complexity, reduced number of different parts, volume discount cost, and ease of interchangeability. However, optical components in the assembly 1-150 utilize rotation about orthogonal axes. For example and referring again to FIG. 2-2A, two optical windows 2-232, 2-237 rotate about axes that are parallel to the X axis shown in the drawing, and can be directly driven by the stepper motors 2-222, 2-224, respectively. In this case, the optical windows can be mounted directly to ends of the motors' drive shafts, for example. On the other hand, two of the optical windows 2-231, 2-235 rotate about axes that are essentially orthogonal to the X axis. Normally, this would require mounting the actuators for these two optical windows 2-231, 2-235 orthogonal to actuators for the other two optical windows 2-232, 2-237, which would appreciably increase the overall height of the beam-shaping and steering assembly 1-150. Alternatively, it may require using a different type of actuator, which would increase the number of components having a different design in the beam-shaping and steering assembly.

To maintain an overall low profile of the beam-shaping and steering assembly, mechanical linkages 2-242, 2-244 may be used that allow all rotary actuators to be mounted such that their drive shafts all lie in approximately a same plane or in approximately parallel planes. An example mechanical linkage 2-242 (which does not require gears, pulleys, or sprockets) that allows such mounting of rotary actuators is depicted in FIG. 2-5A, though other linkages may be used in some embodiments. According to some embodiments, a mechanical linkage may comprise a cam arm 2-510 attached to a rotary drive shaft 2-530 of an actuator, a bearing 2-520 attached to the cam arm, and a lever arm 2-540 connected to an optical mount 2-505. The actuator's shaft 2-530 may rotate about a first axis (e.g., an axis parallel to the X axis shown in the drawing). The optical mount 2-505 may hold an optical window 2-231, for example, and rotate using an axle and/or a bearing 2-550 about a second axis of rotation (e.g., an axis parallel to the Y axis) that is approximately orthogonal to the drive shaft's axis of rotation. When the actuator is operated, the bearing 2-520 presses on the lever arm 2-540 and runs across a surface of the lever arm causing the optical window 2-231 to rotate about the second axis of rotation. A torsion spring 2-560 (or any other suitable spring) backed by a support 2-446 can provide stabilizing counterbalancing force against the actuator pressing on lever arm 2-540 and remove any backlash in the mechanical linkage. In some cases, the support 2-446 may comprise a portion of a lid that is used to cover the beam-shaping and steering assembly 1-150. The mechanical linkage shown in FIG. 2-5A can be used to rotate optical windows, turning mirrors, and/or the image rotation prism in the beam-shaping and steering assembly.

The inventors have recognized and appreciated that the rotational movement of the lever arm 2-540 about the second axis of rotation and the circular trajectory of the bearing 2-520 will normally lead to a nonlinear change in angle of the optical component 2-231 due to a change in angle of the actuator's drive shaft 2-530. According to some embodiments, a curved surface 2-545 may be formed on the lever arm that compensates for the nonlinearities. When a curved surface is employed on the lever arm 2-540, there may be a linear or approximately linear relation between a change in angle of the rotary drive shaft 2-530 and a change in angle of the optical component 2-231 over an extended range of motion of the optical component compared to the case when the contact surface of the lever arm 2-540 is flat. A curvature of the curved surface 2-545 can be engineered to provide a linearized relation for a desired application. Using a curved surface 2-545 can increase the useful range of linearized output (e.g., rotary motion of optical window 2-231)resulting from rotary motion of the rotary actuator. For example, the output may remain linear to within ±5% error over a rotation of 30 degrees about the bearing 2-550. In some implementations, the output may remain linear to within ±2% error over a rotation of 30 degrees about the bearing 2-550. As one example, the lever arm 2-434 of the cradle 2-410, shown in FIG. 2-4, can include a curved surface to linearize a relation be a rotation angle of an actuator that presses a bearing 2-520 on the lever arm 2-434 and a rotation angle of the image rotation prism 2-254.

As another example, a curved surface 2-545 can be engineered to provide a linearized displacement of an optical beam that passes through an optical window 2-231 that is rotated by the mechanical linkage depicted in FIG. 2-5A. Design of the curved surface can take into account rotary motion of the cam arm 2-510, rotary motion of the optical window 2-231, and Snell-Descartes law for an optical beam passing through the optical window. When an appropriately-designed curvature is formed in the lever arm 2-540, linearized displacement can be obtained over an extended range of rotary motion of the cam arm 2-510. An example of linearized beam displacement over an extended range of rotary motion of a cam arm 2-510 is shown in the graph of FIG. 2-5B. A linear fit to the data shows an $R^2$ value of 0.983. Some of the noise in the data points is believed to be due to irregularities in motion of the bearing 2-520 and smoothness of the curved surface 2-545. Higher $R^2$ values are expected with higher quality bearings and more precise machining or finishing of the curved surface 2-545. In embodiments, an engineered curved surface 2-545 can linearize measured output for a mechanical linkage to an $R^2$ value as high as 0.98, though higher values may be obtained in some cases.

Optical components (e.g., anamorphic prisms 2-252, dove prism 2-254, turning mirror 2-234, and optical windows) that are used in the beam-shaping and steering assembly 1-150 may be of moderate or high optical quality. In some embodiments, the optical components may have a surface quality of 40-20 (scratch, dig) or better for surfaces through which the optical beam passes or is reflected from. The flatness of these surfaces may be as high as ¼ of a wavelength at 633 nm or less. Anti-reflection (AR) coatings may be applied to surfaces that the optical beam passes through. The AR coating may be narrowband in some embodiments, or may be broadband in other embodiments. If beams of two wavelengths pass through a surface (e.g., fundamental and second harmonic optical beams), then a dichroic AR coating may be applied to the surface. In some implementations, any coatings used on the optics may be high power coatings, so that the beam-shaping and steering assembly can be used for optical sources that produce output beam powers up to 100 Watts.

An advantageous aspect of the beam-shaping and steering module 1-150 is that incident-angle adjustments to $\theta_x$ and $\theta_y$ (referring to FIG. 1-3) for a beam incident on a receiving optical coupling component can be made substantially independent of X, Y adjustments to the position of the focused beam at the surface 2-340, as explained in connection with FIG. 2-3. Additionally, adjustments to beam rotation or roll φ can be made substantially independent of $\theta_x$, $\theta_y$, X, and Y adjustments. Accordingly, five beam parameters ($\theta_x$, $\theta_y$, X, Y, and φ) can be adjusted essentially independently of each other. For example, adjustment of any one parameter can be made with essentially no cross coupling into the other beam parameters. Further, beam focus on the receiving optical component can be changed essentially independently of other beam characteristics (e.g., by translating lens 2-233). These aspects of independent adjustments can reduce the complexity of alignment of an incident beam to a receiving optical component, and can allow for automated alignment of an optical beam 2-350 to a receiving optical component. For example and referring again to FIG. 1-3, optical energy from an input optical beam having pulses 1-122 that are coupled into one or more waveguides 1-312 via a grating coupler 1-310 or sliced grating coupler 2-100 can be monitored with one or more photodiodes 1-324 at an opposite end of the one or more waveguides during an alignment procedure. Any of the beam's incident angle and rotation angle may be adjusted to increase or optimize coupling without appreciably changing the beam's position on the grating coupler. Additionally, if needed, adjustments to the beam focus may be made independently of adjustments to other beam parameters by moving the lens 2-233 along the optical beam path. Because adjustments to beam parameters are essentially decoupled from one another, the beam-shaping and steering assembly 1-150 may be used to more readily automate alignment of an optical beam from an optical source 1-110 to a hi-tech system 1-160 and to increase and maintain high coupling efficiency. If adjustments to one beam parameter (e.g., X position) cross-coupled into one or more other beam parameters (e.g., incident angle or beam shape), alignment would be more complicated and difficult to automate.

According to some embodiments, an automated alignment procedure may be used to align the optical beam from an optical source 1-110 to a waveguide coupler (e.g., sliced grating coupler 2-100) in a hi-tech system 1-160. An alignment procedure may comprise executing a spiral search for the grating coupler 2-100, as depicted in FIG. 2-6, though other types of search patterns such as raster-scan and boustrophedonic scanning may be used. The spiral search may be executed by rotating the third optical window 2-235 and the fourth optical window 2-237 to laterally translate a focused beam 2-350 in the X and Y directions on the surface of the chip. For example, after a chip 1-140 is loaded into a hi-tech instrument 1-100 and the optical source 1-110 is turned on, the optical beam may strike the surface of the chip at the location marked "A" in FIG. 2-6. At this location, there may be no signal detected by the quad detector 1-320. A spiral search path 2-610 may be executed, while signals from the quad detector are monitored. At location "B" the quad detector may begin to register (X, Y) position signals of the beam from its detectors. Control circuitry may then determine the location of the beam with respect to a center of the quad detector, cancel execution of the spiral path, and operate the actuators 2-223 and 2-224 to steer the beam to a center of the quad detector 1-320, point "C." The grating coupler 2-100 may be located approximately centrally over the quad detector. Subsequently, fine position, beam rotation, and incident angle adjustments may be made to increase an amount of optical power coupled into the waveguides 2-120 and to improve the uniformity of power coupled into each waveguide. In some embodiments, the optical powers from multiple integrated photodiodes 1-324 coupled to multiple waveguides 2-120 may be monitored to aid in making fine adjustments to the optical beam at the grating coupler for improving uniformity of the powers coupled into the multiple optical waveguides.

Other methods and apparatus may be used to search for the quad detector 1-320 and align the focused beam 2-350 to the grating coupler 2-100. In some embodiments, the sensitivity of the quad detector 1-320 can be improved to expand the range over which the optical beam may be detected. For example, signals from the quad detector with the optical beam power at a high power (e.g., fully on) may be compared against signals from the quad detector with the optical beam power at a low setting (e.g., off). Additionally, the signals may be integrated over longer periods of time to improve the location-detection sensitivity of the quad detector, when the optical beam may be located at an appreciable distance from the quad detector.

In some embodiments, light scattering elements 2-630 can be fabricated on the chip 1-140 around the quad detector 1-320. When the focused beam is misaligned and at a peripheral location away from the quad detector, the scattering elements may scatter light from the focused beam towards the quad detector 1-320. The detected scattered light may then indicate a position of the beam.

In some implementations, a narrow, linear scattering element (e.g., a trench or rib, an array of posts or divots, not shown) or a line detector, similar in width to the anticipated focused beam size, may be placed through the center of or to the side of the quad detector (or in any suitable orientation with respect to the quad detector), and extend significantly beyond opposite edges of the quad detector (e.g., to a distance greater than a reasonable expectation of initial beam offset error). Since the orientation of this element or detector is known by design, the focused beam 2-350 can first be scanned in a direction perpendicular to the element until the beam strikes the element or detector and is positively detected, either by scatter to the quad detector 1-320, or directly by the line detector. Then, the beam may be scanned in the other direction to find the quad detector 1-320.

According to some embodiments, an optical beam may be initially expanded at the surface 2-340 of the chip 1-140 (e.g., defocusing the beam by moving lens 2-233 with an actuator, inserting a defocusing lens in the beam path, or using other means). The footprint of the beam on the chip may then be greatly increased (e.g., by a factor of 10 or more) so that any scanning process can use larger steps between beam positions when searching for the quad detector 1-320 (e.g., larger offsets between radial loops on a spiral scan). This and the foregoing alternative searching methods may reduce the search time associated with aligning the focused beam 2-350 to the grating coupler 2-100.

After alignment, the focused optical beam may be maintained actively in an aligned position. For example, an (X, Y) position of the beam determined after the initial alignment with respect to the quad detector 1-320 may be actively maintained using feedback from the quad detector and activation of the actuators 2-223 and 2-224 to maintain the beam in an approximately fixed location. In some embodiments, incident angles of the optical beam at the surface may not be adjusted after an initial alignment to optimize power coupled into the waveguide. Additionally, an amount of power coupled into the waveguides may be maintained at approximately a constant level throughout measurements.

According to some embodiments, power delivered to the waveguides 2-120 may be maintained at approximately constant levels by using feedback to control optical components of the beam-shaping and steering assembly 1-150 and/or optical or other components within the optical source 1-110. For example, one or more photodiode 1-324 signals from photodiodes arranged to receive light from one or more of the waveguides may be monitored by a signal processor to evaluate power levels coupled to the waveguides. Control signals may be produced in response to detected changes in power levels at the waveguides, and the control signals may be applied to actuators in the beam-shaping and steering assembly and/or optical source. With regard to an optical source comprising a laser that produces a frequency-doubled output beam using a frequency-doubling crystal, a control signal may be applied to an actuator that controls an orientation of a half-wave plate in the optical source. Rotation of the half wave plate may change the polarization of optical pulses entering the frequency-doubling crystal, and therefor change the conversion efficiency to and power of the frequency-doubled wavelength. This could control optical power without affecting stability of the optical source or having to misalign the optical beam with respect to the grating coupler 2-100.

Example circuitry for beam alignment and power stabilization is depicted in FIG. 2-7, according to some embodiments. A quad detector 1-320 is represented as four photodiodes, and a waveguide photodiode 1-324 is represented as a fifth photodiode. In some implementations, there may be a large plurality of waveguides 2-120 to which optical power is coupled from a single grating coupler. Accordingly, there may be a large plurality of waveguide photodiodes 1-324 arranged to receive radiation from the waveguides that have signal outputs connected to control circuitry 2-730. Amplifying circuitry 2-710 may be arranged to detect voltages produced by photoconduction of the diodes. The amplifying circuitry 2-710 may comprise CMOS electronics (e.g., FETs, sampling circuits, analog-to-digital converters) that convert an analog signal to a digital signal, according to some embodiments. In other embodiments, analog signals may be provided from the amplifying circuitry to control circuitry 2-730.

In some embodiments, control circuitry may comprise one or a combination of the following elements: analog and digital circuitry, an ASIC, an FPGA, a DSP, a microcontroller, and a microprocessor. The control circuitry 2-730 may be configured to process signals received from the one or more waveguide photodiodes to determine a level of optical power in each waveguide. Control circuitry 2-730 may be further configured to process received signals from the quad detector 1-320 to determine an (X, Y) location of the optical beam with respect to the quad detector. In some implementations, the control circuitry 2-730 is configured to detect power coupled into each waveguide, and provide a control signal to the actuators to move the optical beam such that power is equalized in the waveguides or has a highest uniformity across the waveguides.

A position of the optical beam in the X direction may be determined, for example, by control circuitry 2-730 adapted to execute the following algorithm:

$$S_x = [(V_{Q1} + V_{Q4}) - (V_{Q2} + V_{Q3})]/V_T$$

where $S_x$ is a normalized signal level corresponding to the x direction, $V_{Qn}$ is a signal level (e.g., voltage) received from the $n^{th}$ photodiode of the quad detector, and $V_T$ is a total signal level received by summing the signal from all four photodiodes. Additionally, a position of the optical beam in the Y direction may be determined, for example, using the following algorithm:

$$S_y = [(V_{Q3} + V_{Q4}) - (V_{Q1} + V_{Q2})]/V_T.$$

An average power coupled into all waveguides on the chip 1-140 may be determined by summing signals from all of the photodiodes 1-324 arranged to detect power in each of the waveguides on the chip.

Control signals may be generated by control circuitry 2-730 responsive to a detected beam position in X and Y and responsive to power levels detected in one or more waveguides 2-120. The control signals may be provided as digital signals over one or more communication links (SM1, SM2, SM5) to actuators of the beam-shaping and steering module 1-150 and over one or more communication links WP to actuators or controls of the optical source system 1-110 (e.g., an actuator arranged to rotate a half-wave plate or beam attenuator, a control for applying electrical power to a diode optical source). The control signals may be applied to stabilize power and/or improve optical coupling between the optical source 1-110 and hi-tech system 1-160.

As may be appreciated from the foregoing description, the beam-shaping and steering assembly 1-150 may advantageously not include some beam-shaping and steering components that would significantly increase cost. Such components include electro-optical and thermo-optic components, phased array or beam-combining components, and micro-electrical-mechanical systems. According to some embodiments, all parts of a beam-shaping and steering assembly 1-150 may be manufactured using standard machining and molding capabilities.

Although use of the beam-shaping and steering assembly is described primarily for coupling to a sliced grating coupler, it may be used to couple an optical beam to other optical systems such as, but not limited to, an optical fiber, a two-dimensional fiber array, an integrated optical waveguide via butt coupling, one or more microfluidic channels, a prism coupler, or an optical system arranged to excite surface plasmons.

Some embodiments of a beam-shaping and steering assembly 1-150 may include sensors and circuitry (neither shown in FIG. 2-2A) for monitoring and evaluating the operational status of at least some components in the assembly. For example, a beam-shaping and steering assembly 1-150 may include a printed circuit board that includes circuitry to monitor the health and/or operation of beam steering components (e.g., operational status of actuators, motion of optical components) and includes control circuitry for operating the actuators. In some cases, a PCB may include a microcontroller and/or control circuitry 2-730 that provides for processing received signals and outputting control signals to the actuators based on the processed received signals. Sensors for monitoring motion of the components may include optical encoders, mechanical encoders, optical proximity switches, and limit switches (for monitoring mechanical motion of components to determine if they move as instructed). In some cases, motion of an optical component can be determined from an amount of current supplied to an actuator that operates on the optical component. In some embodiments, temperature sensors and/or current sensors (e.g., thermistors) may be used to monitor electronic components in the assembly (e.g., stepper motors or other actuators) to determine if they are operating within safe operating temperatures or to determine any temperature-compensating adjustments to optical component positions to cancel temperature effects on beam characteristics.

In some embodiments, one or more photodiodes, one or more imaging arrays, and/or one or more quad detectors may be incorporated in the beam-shaping and steering assembly 1-150 to monitor characteristics of the optical beam 2-350 at one or more locations within the assembly. Characteristics that could be monitored include, but are not limited to, power in a fundamental beam, power in a second harmonic beam, output beam position, output beam pointing direction, output beam shape, and output beam pointing angle. For example, a photodiode can be used to monitor an amount of energy in the fundamental beam or another beam at a beam dump 2-260 when beams of different wavelengths are separated. A second photodiode could monitor an amount of power in a second harmonic beam of fundamental beam that leaks through a turning mirror (e.g., mirror 2-234) or reflects from a facet of an optical window 2-231, 2-232, 2-235, 2-237 or lens 2-233, or other optical component within the assembly 1-150. In some cases, a photodiode can be mounted in a cover placed over the chassis 2-210 or in the chassis base to receive a facet reflection from and optical window. In some cases, optical power from a fundamental and/or second harmonic beam can be used to evaluate health of an optical source (e.g., stability of a mode-locked laser that provides and input beam 2-205). In embodiments, a signal generated from a photodiode that detects a mode-locked laser beam can be used to generate a clock signal that is phase locked to in time to pulse arrival times at the photodiode.

A quad detector or imaging array could be used to monitor the location and/or presence of one or more stray reflected beams from a facet of an optical component within the beam-shaping and steering assembly or from an optical component located downstream of the assembly. As an example and referring to FIG. 2-3, a quad detector or imaging array could be mounted at a position with respect to an optical window 2-231, 2-232, 2-235, 2-237 to detect and monitor a position and/or beam shape of a low-level facet refection from the optical window. An output from one or more quad detectors and/or imaging arrays arranged in such a manner could be used to help stabilize an outgoing beam's position, shape, rotation angle $\phi$, and pointing angle.

Signals from the electrical, thermal, and optical sensor(s) may be provided to signal processing logic (e.g., a microcontroller and/or logic chips) on a PCB that is provided with the beam-shaping and steering assembly 1-150 to determine whether the beam-shaping and steering assembly is operating stably and as expected and to produce error signals if the assembly is malfunctioning. In some implementations, the PCB may be mounted to the chassis 2-210 of the beam-shaping and steering assembly, though in other embodiments, the PCB may be located elsewhere and connect to the sensors, actuators, and any other electronics within the assembly 1-150 via a multi-wire cable.

Embodiments of the described technology include at least the configurations and methods set forth in (1) through (51) below.

(1) A beam-shaping and steering assembly comprising a first optical component arranged to transform a first transverse beam shape of an input beam into a second transverse beam shape of a second beam; a second optical component arranged to rotate the second transverse beam shape about an optical axis of the second beam; and a third optical component arranged to adjust one of: a first position or a first directional angle of an output beam at a target location.

(2) The beam-shaping and steering assembly of configuration (1), wherein displacements of the input beam of up to ±3 mm through the first optical component do not change the second transverse beam shape.

(3) The beam-shaping and steering assembly of configurations (1) or (2), wherein the first optical component comprises an anamorphic prism pair.

(4) The beam-shaping and steering assembly of any one of configurations (1) through (3), further comprising a beam dump, wherein the first optical component spatially separates optical wavelengths in the input beam and the beam dump is located to receive an output from the first optical component at a first wavelength.

(5) The beam-shaping and steering assembly of configuration (4), further comprising a turning mirror arranged to receive the second beam having a second wavelength and direct the second beam to the third optical component.

(6) The beam-shaping and steering assembly of any one of configurations (1) through (5), wherein the second optical component comprises a dove prism.

(7) The beam-shaping and steering assembly of any one of configurations (1) through (6), wherein the third optical component comprises an optical window.

(8) The beam-shaping and steering assembly of any one of configurations (1) through (7), further comprising a chassis supporting the first optical component, the second optical component, and the third optical component, wherein the chassis is mounted in an instrument comprising a printed circuit board (PCB) on which is mounted a device having a receiving optical component that receives the second beam, wherein a region of the PCB containing the device attaches to the chassis to reduce motion of the device with respect to the beam-shaping and steering assembly.

(9) The beam-shaping and steering assembly of any one of configurations (1) through (8), further comprising a fourth optical component arranged to adjust one of: a second position or a second directional angle of the output beam at the target location.

(10) The beam-shaping and steering assembly of configuration (9), wherein first effects on the output beam at the target location caused by adjustments to the fourth optical component have essentially no effect on second effects on the output beam at the target location caused by adjustments to the third optical component and vice versa.

(11) The beam-shaping and steering assembly of configurations (9) or (10), further comprising a first actuator coupled to the third optical component; and a second actuator coupled to the fourth optical component, wherein the first actuator and the second actuator each include a rotary drive shaft that are essentially parallel to a same plane.

(12) The beam-shaping and steering assembly of configuration (11), wherein the rotary drive shafts of the first actuator and the second actuator are essentially parallel.

(13) The beam-shaping and steering assembly of configurations (11) or (12), wherein changes to the output beam at the target location effected by the third optical component are in a dimension that is essentially orthogonal to changes to the output beam at the target location effected by the fourth optical component.

(14) The beam-shaping and steering assembly of any one of configurations (1) through (13), wherein the third optical component is arranged to adjust the first directional angle of the output beam at the target location, the beam-shaping and steering assembly further comprising a fourth optical component arranged to adjust a second directional angle of the output beam at the target location; a fifth optical component arranged to adjust the first position of the output beam at the target location; and a sixth optical component arranged to adjust a second position of the output beam at the target location.

(15) The beam-shaping and steering assembly of configuration (14), further comprising a focusing lens arranged such that the third and fourth optical components are disposed on a first side of the focusing lens and the fifth and sixth optical components are disposed on a second side of the focusing lens.

(16) The beam-shaping and steering assembly of configurations (14) or (15), wherein the first directional angle is a pitch angle of the output beam at the target location; the second directional angle is a yaw angle of the output beam at the target location; the first position is an X-direction position of the output beam at the target location; and the second position is a Y-direction position of the output beam at the target location, the X-direction and Y-direction being orthogonal.

(17) The beam-shaping and steering assembly of any one of configurations (1) through (16), wherein the second transverse beam shape is substantially elliptical and the first transverse beam shape is substantially circular.

(18) A method of coupling a beam from an optical source to a receiving optical component of a system, the method comprising acts of receiving, by a beam-shaping and steering assembly, the beam from the optical source; transforming, with the beam-shaping and steering assembly, a first transverse beam shape of the beam to a second transverse beam shape of an output beam; positioning, with the beam-shaping and steering assembly, the output beam on the receiving optical component; and adjustably rotating, with the beam-shaping and steering assembly, the second transverse beam shape.

(19) The method of (18), wherein the rotating is performed by rotating an optical component made from a single piece of material.

(20) The method of (18) or (19), wherein the first transverse beam shape is round and the second transverse beam shape is elliptical.

(21) The method of any one of (18) through (20), further comprising changing, with the beam-shaping and steering assembly, one or both of an incident angle and a position of the output beam on the receiving optical component.

(22) The method of any one of (18) through (21), wherein rotation of an optical window is used to adjust incident angle of the output beam on the receiving optical component.

(23) The method of any one of (18) through (22), wherein a transverse size of the output beam is between 10% and 35% larger than a coupling region of the receiving optical component and is oriented at a roll angle with respect to the receiving optical component.

(24) The method of (23), further comprising adjusting a position of the output beam at the receiving optical component to compensate for an asymmetry of intensity in the second transverse beam shape.

(25) The method of any one of (18) through (24), wherein the receiving optical component comprises a sliced grating coupler configured to couple the output beam to a plurality of waveguides.

(26) The method of (25), further comprising adjusting, with the beam-shaping and steering assembly, a uniformity of power coupled to the plurality of waveguides.

(27) An optical system for coupling a beam of radiation to an apparatus, the optical system comprising three rotary actuators; and three optical components coupled respectively to the three rotary actuators, wherein each rotary actuator has a drive shaft that rotates about a shaft axis to move an optical component of the three optical components, wherein the shaft axes of the three rotary actuators are essentially parallel to a same plane, and wherein actuation of the three optical components by the three rotary actuators alters the beam in three different degrees of freedom.

(28) The optical system of configuration (27), wherein couplings between the three optical components and the three rotary actuators do not include gears, pulleys, or sprockets.

(29) The optical system of configurations (27) or (28), wherein at least two of the three optical components are transparent optical windows and at least two of the drive shafts are essentially parallel.

(30) The optical system of any one of configurations (27) through (29), wherein the three rotary actuators have essentially a same size and structure.

(31) The optical system of any one of configurations (27) through (30), wherein movement of a first optical component of the three optical components by a first rotary actuator of the three rotary actuators rotates the transverse beam shape at a location exiting the first optical component about an optical axis that runs centrally along the beam exiting the first optical component.

(32) The optical system of configuration (31), wherein movement of the first optical component rotates the beam at the target location about an optical axis that runs centrally along the focused beam with essentially no lateral displacement of the focused beam at the target location.

(33) The optical system of any one of configurations (27) through (32), further comprising a lens to focus the beam to a target location in the apparatus, wherein movement of two optical components of the three optical components by two rotary actuators of the three rotary actuators alters incident angles of the focused beam at the target location with essentially no lateral displacement of the focused beam at the target location.

(34) The optical system of configuration (33), further comprising a fourth optical component coupled to a fourth rotary actuator having a drive shaft that rotates about a shaft axis to move the fourth optical component; and a fifth optical component coupled to a fifth rotary actuator having a drive shaft that rotates about a shaft axis to move the fifth optical component, wherein the shaft axes of the fourth and fifth rotary actuators are essentially parallel to the same plane.

(35) The optical system of configuration (34), wherein the shaft axes of the three rotary actuators and fourth and fifth rotary actuators lie essentially in the same plane.

(36) The optical system of configurations (34) or (35), wherein the optical system has a height no greater than 40 mm. (37) The optical system of any one of configurations (34) through (36), wherein movement of the fourth and fifth optical components laterally translate the focused beam at the target location in two degrees of freedom with essentially no changes in incident angles of the beam at the target location.

(38) The optical system of any one of configurations (27) through (37), further comprising a beam-shaping component configured to convert a received round beam shape to an elongated beam shape.

(39) The optical system of configuration (38), wherein the beam-shaping component is further configured to spatially separate different radiation wavelengths in the beam.

(40) An optical system for coupling a beam of radiation to an apparatus, the optical system comprising a first optical component supported in an adjustable mount; and a first actuator coupled to the adjustable mount, wherein movement of the first optical component by the first actuator rotates a transverse shape and polarization of an exit beam that exits the first optical component, wherein the rotation of the transverse shape and polarization are about an optical axis that runs centrally along the exit beam.

(41) The optical system of configuration (40), wherein the first optical component is made of a single piece of material that is aligned so that the beam is incident centrally along an axis of rotation of the first optical component.

(42) The optical system of configurations (40) or (41), further comprising a second optical component arranged to transform a first transverse beam shape of the beam into a second transverse beam shape of a second beam and to spatially separate wavelengths in the beam; and a beam dump arranged to receive a spatially separated wavelength from the beam.

(43) The optical system of any one of configurations (40) through (42), further comprising an additional optical component arranged to adjust a directional angle of the exit beam.

(44) The optical system of configuration (43), wherein the additional optical component is a transparent optical window.

(45) An optical system for altering a beam of radiation, the optical system comprising a first optical component supported by an adjustable mount that is configured to rotate the first optical component about a first axis; a rotary actuator having a drive shaft that rotates about a second axis that is not parallel to the first axis; a cam arm connected to the drive shaft a bearing connected to the cam arm; and a curved surface connected to the adjustable mount, wherein the bearing runs across the curved surface when the rotary actuator is actuated to rotate the first optical component.

(46) The optical system of configuration (45), wherein the curved surface is shaped to linearize a change in a parameter of an optical beam passing through the optical component due to rotation of the cam arm by the drive shaft.

(47) An optical beam-steering apparatus comprising a first rotary actuator arranged to rotate a first optical window; a second rotary actuator arranged to rotate a second optical window; and a lens, wherein rotation of the first optical window adjusts a lateral position of an optical beam at a target location and rotation of the second optical window adjusts an incident angle of the beam at the target location without changing the lateral position by more than 10 microns.

(48) The optical beam-steering apparatus of configuration (47), wherein a rotary drive shaft of the first rotary actuator is essentially parallel to a rotary drive shaft of the second rotary actuator.

(49) An optical beam-steering apparatus comprising three rotatable transparent optical windows arranged to adjust three parameters of an output beam from the beam-steering apparatus in three orthogonal degrees of freedom.

(50) The optical beam-steering apparatus of configuration (49), further comprising three rotary actuators configured to rotate the three rotatable transparent optical windows, wherein drive shafts of the three rotary actuators are essentially parallel to a same plane.

(51) The optical beam-steering apparatus of configuration (50), wherein the drive shafts are essentially parallel to each other.

VI. Conclusion

Having thus described several aspects of several embodiments of a beam-shaping and steering assembly, it is to be appreciated that various alterations, modifications, and improvements will readily occur to those skilled in the art. Such alterations, modifications, and improvements are intended to be part of this disclosure, and are intended to be within the spirit and scope of the invention. While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

For example, embodiments may be modified to include more or fewer optical components in the beam-shaping and steering assembly than described above. Moreover, optical configurations may differ from those shown with some beam-shaping and steering assemblies have more or fewer turns or folds in an optical path passing through the assembly.

While various inventive embodiments have been described and illustrated, those of ordinary skill in the art will readily envision a variety of other means and/or structures for performing the function and/or obtaining the results and/or one or more of the advantages described, and each of such variations and/or modifications is deemed to be within the scope of the inventive embodiments described. More generally, those skilled in the art will readily appreciate that all parameters, dimensions, materials, and configurations described are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure may be directed to each individual feature, system, system upgrade, and/or method described. In addition, any combination of two or more such features, systems, and/or methods, if such features, systems, system upgrade, and/or methods are not mutually inconsistent, is included within the inventive scope of the present disclosure.

Further, though some advantages of the present invention may be indicated, it should be appreciated that not every embodiment of the invention will include every described advantage. Some embodiments may not implement any features described as advantageous. Accordingly, the foregoing description and drawings are by way of example only.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used are for organizational purposes only and are not to be construed as limiting the subject matter described in any way.

Also, the technology described may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used, should be understood to control over dictionary definitions, definitions in documents incorporated by reference, and/or ordinary meanings of the defined terms.

Numerical values and ranges may be described in the specification and claims as approximate or exact values or ranges. For example, in some cases the terms "about," "approximately," and "substantially" may be used in reference to a value. Such references are intended to encompass the referenced value as well as plus and minus reasonable variations of the value. For example, a phrase "between about 10 and about 20" is intended to mean "between exactly 10 and exactly 20" in some embodiments, as well as "between 10±δ1 and 20±δ2" in some embodiments. The amount of variation δ1, δ2 for a value may be less than 5% of the value in some embodiments, less than 10% of the value in some embodiments, and yet less than 20% of the value in some embodiments. In embodiments where a large range of values is given, e.g., a range including two or more orders of magnitude, the amount of variation δ1, δ2 for a value could be as high as 50%. For example, if an operable range extends from 2 to 200, "approximately 80" may encompass values between 40 and 120 and the range may be as large as between 1 and 300. When only exact values are intended, the term "exactly" is used, e.g., "between exactly 2 and exactly 200." The term "essentially" is used to indicate that values are the same or at a target value or condition to within ±3%.

The term "adjacent" may refer to two elements arranged within close proximity to one another (e.g., within a distance that is less than about one-fifth of a transverse or vertical dimension of a larger of the two elements). In some cases there may be intervening structures or layers between adjacent elements. In some cases adjacent elements may be immediately adjacent to one another with no intervening structures or elements.

The indefinite articles "a" and "an," as used in the specification and in the claims, unless clearly indicated to the contrary, should be understood to mean "at least one."

The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

The invention claimed is:

1. A beam-shaping and steering assembly comprising:
   a first optical component arranged to transform a first transverse beam shape of an input beam into a second transverse beam shape of a second beam;
   a second optical component arranged to rotate the second transverse beam shape about an optical axis of the second beam; and
   a third optical component arranged to adjust one of: a first position of an output beam at a target location or a first incidence angle of a center of the output beam at the target location.

2. The beam-shaping and steering assembly of claim 1, wherein displacements of the input beam of up to ±3 mm through the first optical component do not change the second transverse beam shape.

3. The beam-shaping and steering assembly of claim 1, wherein the first optical component comprises an anamorphic prism pair.

4. The beam-shaping and steering assembly of claim 1, further comprising a beam dump, wherein the first optical component spatially separates optical wavelengths in the input beam and the beam dump is located to receive an output from the first optical component at a first wavelength.

5. The beam-shaping and steering assembly of claim 4, further comprising a turning mirror arranged to receive the second beam having a second wavelength and direct the second beam to the third optical component.

6. The beam-shaping and steering assembly of claim 1, wherein the second optical component comprises a dove prism.

7. The beam-shaping and steering assembly of claim 1, wherein the third optical component comprises an optical window.

8. The beam-shaping and steering assembly of claim 1, further comprising a chassis supporting the first optical component, the second optical component, and the third optical component, wherein the chassis is mounted in an instrument comprising a printed circuit board (PCB) on which is mounted a device having a receiving optical component that receives the second beam, wherein a region of the PCB containing the device attaches to the chassis to reduce motion of the device with respect to the beam-shaping and steering assembly.

9. The beam-shaping and steering assembly of claim 1, further comprising a fourth optical component arranged to adjust one of: a second position or a second incidence angle of the output beam at the target location.

10. The beam-shaping and steering assembly of claim 9, wherein first effects on the output beam at the target location caused by adjustments to the fourth optical component have essentially no effect on second effects on the output beam at the target location caused by adjustments to the third optical component and vice versa.

11. The beam-shaping and steering assembly of claim 9, further comprising:
   a first actuator coupled to the third optical component; and
   a second actuator coupled to the fourth optical component,
   wherein the first actuator and the second actuator each include a rotary drive shaft that are essentially parallel to a same plane.

12. The beam-shaping and steering assembly of claim 11, wherein the rotary drive shafts of the first actuator and the second actuator are essentially parallel.

13. The beam-shaping and steering assembly of claim 11, wherein changes to the output beam at the target location effected by the third optical component are in a dimension that is essentially orthogonal to changes to the output beam at the target location effected by the fourth optical component.

14. The beam-shaping and steering assembly of claim 1, wherein the third optical component is arranged to adjust the first incidence angle of the output beam at the target location, the beam-shaping and steering assembly further comprising:
   a fourth optical component arranged to adjust a second incidence angle of the output beam at the target location;

a fifth optical component arranged to adjust the first position of the output beam at the target location; and a sixth optical component arranged to adjust a second position of the output beam at the target location.

15. The beam-shaping and steering assembly of claim 14, further comprising a focusing lens arranged such that the third and fourth optical components are disposed on a first side of the focusing lens and the fifth and sixth optical components are disposed on a second side of the focusing lens.

16. The beam-shaping and steering assembly of claim 14, wherein:

the first incidence angle is a pitch angle of the output beam at the target location;

the second incidence angle is a yaw angle of the output beam at the target location;

the first position is an X-direction position of the output beam at the target location; and the second position is a Y-direction position of the output beam at the target location, the X-direction and Y-direction being orthogonal.

17. The beam-shaping and steering assembly of claim 1, wherein the second transverse beam shape is substantially elliptical and the first transverse beam shape is substantially circular.

18. An optical beam-steering apparatus comprising:

a first rotary actuator arranged to rotate a first optical window;

a second rotary actuator arranged to rotate a second optical window; and a lens, wherein rotation of the first optical window adjusts a lateral position of an optical beam at a target location and rotation of the second optical window adjusts an incident angle of the beam at the target location without changing the lateral position by more than 10 microns.

19. The optical beam-steering apparatus of claim 18, wherein a rotary drive shaft of the first rotary actuator is essentially parallel to a rotary drive shaft of the second rotary actuator.

* * * * *